US007351211B2

(12) United States Patent
Buehlmann et al.

(10) Patent No.: US 7,351,211 B2
(45) Date of Patent: *Apr. 1, 2008

(54) TISSUE LOCALIZING AND SEPARATING ASSEMBLY

(75) Inventors: Eric L. Buehlmann, Redwood City, CA (US); Lisanne A. Eng, San Mateo, CA (US); Christine P. Ventura, San Jose, CA (US); Robert J. Laird, Pinole, CA (US); Frank Ingle, Palo Alto, CA (US)

(73) Assignee: Artemis Medical, Inc., Hayward, CA (US)

( * ) Notice: Subject to any disclaimer, the term of this patent is extended or adjusted under 35 U.S.C. 154(b) by 17 days.

This patent is subject to a terminal disclaimer.

(21) Appl. No.: 11/245,625

(22) Filed: Oct. 7, 2005

(65) Prior Publication Data

US 2006/0030846 A1  Feb. 9, 2006

Related U.S. Application Data

(63) Continuation of application No. 10/374,583, filed on Feb. 25, 2003, now Pat. No. 6,994,677.

(51) Int. Cl.
*A61B 10/00* (2006.01)
*A61B 18/14* (2006.01)
(52) U.S. Cl. .................. 600/567; 606/45; 606/47
(58) Field of Classification Search ............. 606/32, 606/39, 40, 41, 45, 46, 48–50; 600/567
See application file for complete search history.

(56) References Cited

U.S. PATENT DOCUMENTS 4,611,594 A    9/1986  Grayhack
4,638,802 A    1/1987  Okada
4,997,435 A    3/1991  Demeter
5,031,634 A    7/1991  Simon (Continued)

FOREIGN PATENT DOCUMENTS

GB    2020557    11/1979

(Continued)

OTHER PUBLICATIONS

"Anchor Guide Localization and Fixation Device," 2001, SenoRs, Inc.

(Continued)

*Primary Examiner*—Lee S. Cohen
(74) *Attorney, Agent, or Firm*—Welsh & Flaxman LLC

(57) ABSTRACT

A tissue separator assembly has an elongate tubular member and a tissue separator device located at a distal end of the elongate tubular member. An elongate coupler extends through the lumen of the elongate tubular member and has a distal coupler end. A tissue localization assembly has an elongate member and a localization device located at the distal end of the elongate member. The localization device may be movable from a first, radially-contracted state to a second, radially-expandable state. The distal coupler end of the elongate coupler and the proximal end of the elongate tubular member of the localization assembly are joinable to one another to permit docking of the tissue localization assembly to the tissue separator assembly. Methods of use of this device are also described.

14 Claims, 21 Drawing Sheets

U.S. PATENT DOCUMENTS

| | | |
|---|---|---|
| 5,100,423 A | 3/1992 | Fearnot |
| 5,102,415 A | 4/1992 | Guenther |
| 5,190,561 A | 3/1993 | Graber |
| 5,370,647 A | 12/1994 | Graber |
| 5,415,656 A | 5/1995 | Tihon |
| 5,709,697 A | 1/1998 | Ratcliff |
| 5,728,133 A | 3/1998 | Kontos |
| 5,794,626 A | 8/1998 | Kieturakis |
| 5,795,308 A | 8/1998 | Russin |
| 5,796,045 A | 8/1998 | Lancien |
| 6,136,014 A | 10/2000 | Sirimanne |
| 6,179,860 B1 | 1/2001 | Fulton |
| 6,221,006 B1 | 4/2001 | Dubrul |
| 6,258,115 B1 | 7/2001 | Dubrul |
| 6,277,083 B1 | 8/2001 | Eggers |
| 6,280,450 B1 | 8/2001 | McGuckin |
| 6,331,166 B1 | 12/2001 | Burbank |
| 6,344,026 B1 | 2/2002 | Burbank |
| 6,440,147 B1 | 8/2002 | Lee |
| 2002/0007130 A1 | 1/2002 | Burbank |

FOREIGN PATENT DOCUMENTS

| | | |
|---|---|---|
| GB | 2311468 | 1/1997 |
| WO | WO 95/02370 | 1/1995 |

OTHER PUBLICATIONS

"Does your breast care facility address its diagnostic needs," 2000, Neothermia Corp.

PCT Search Report for PCT/US04/05546, dated Nov. 2, 2005.

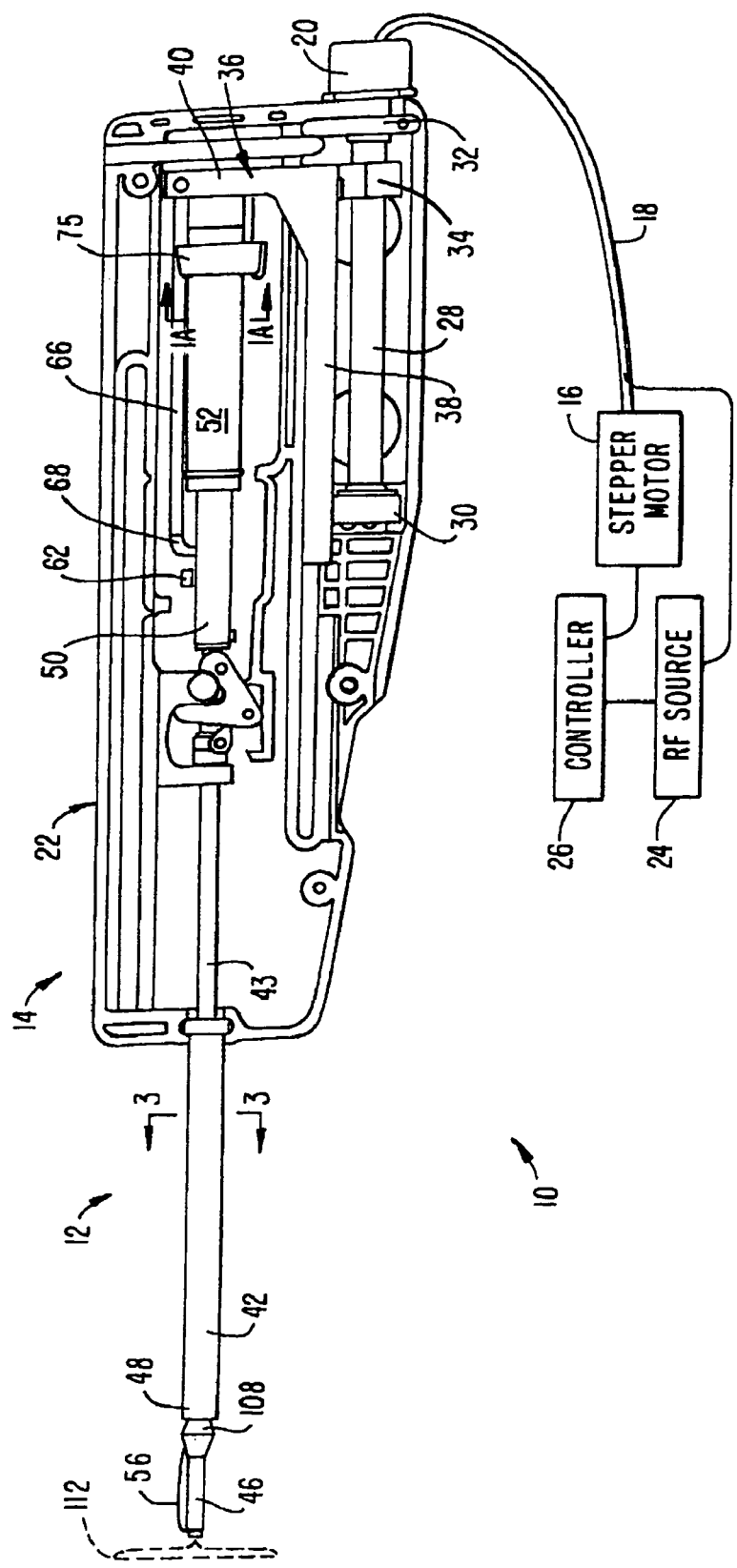
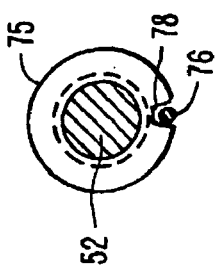
FIG. 1.
FIG. 1A.

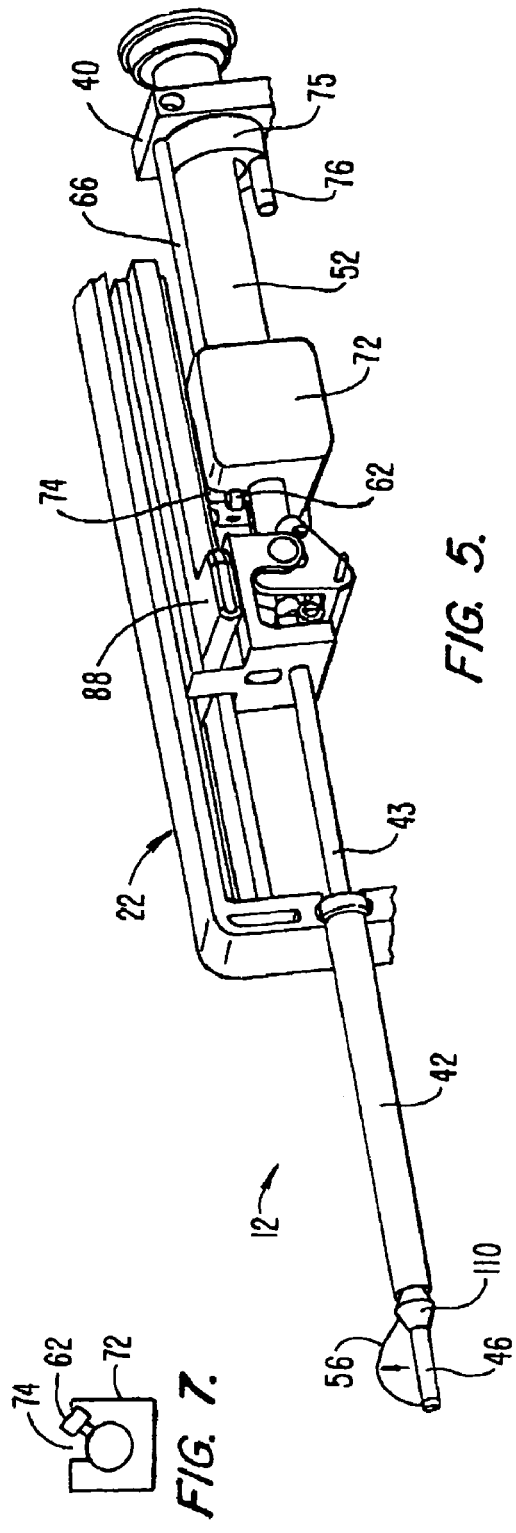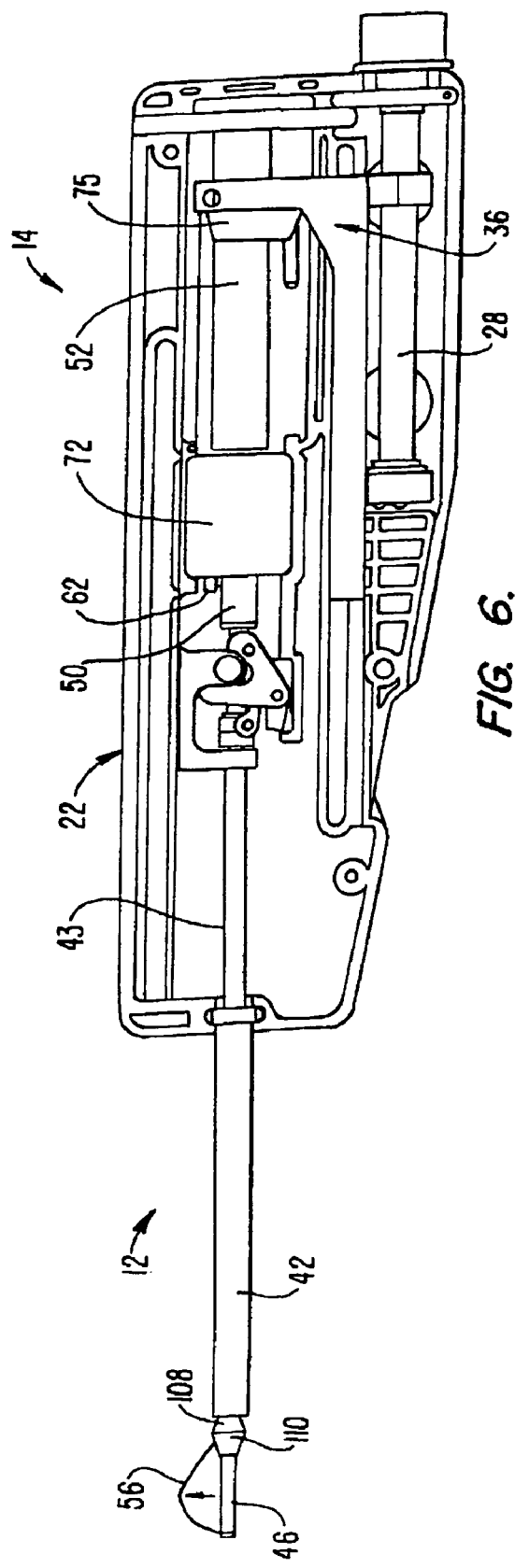

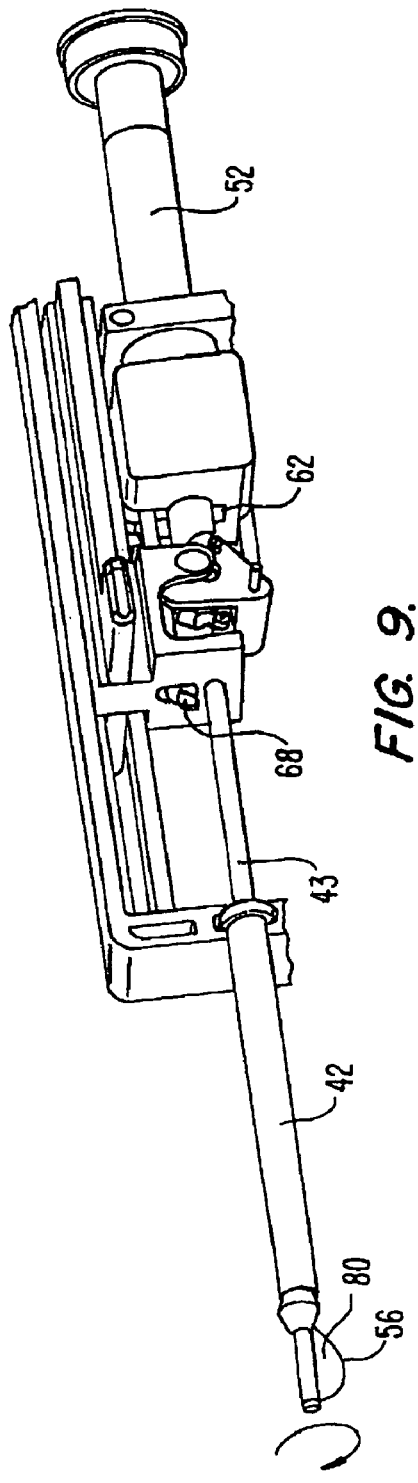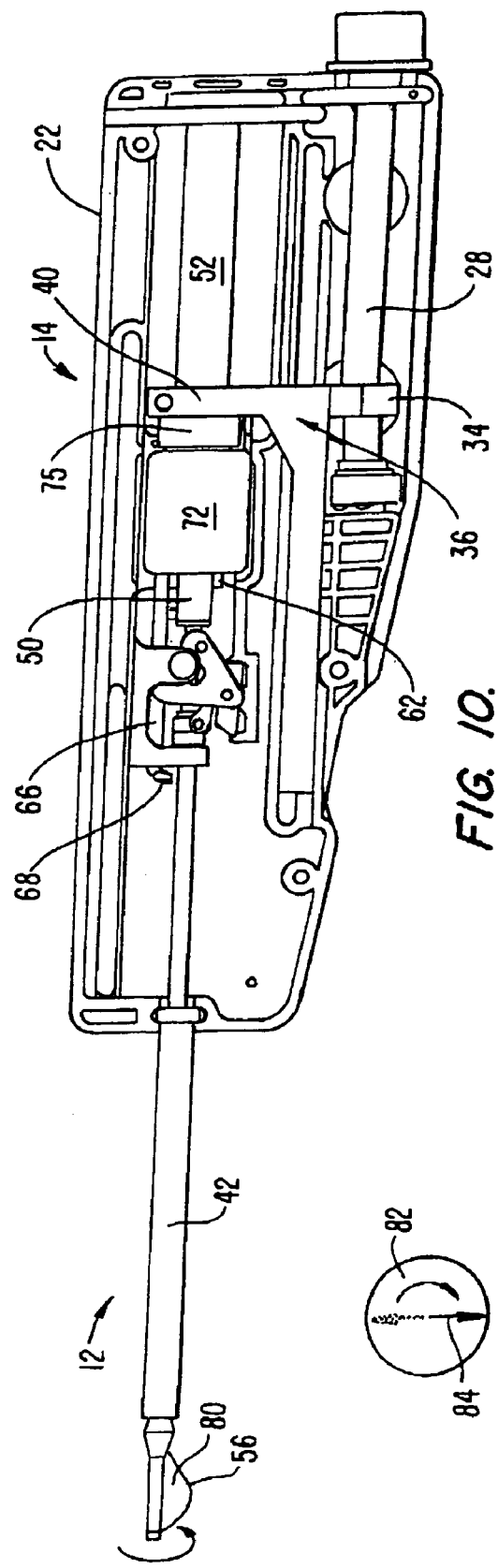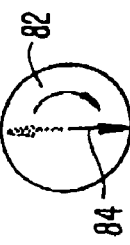

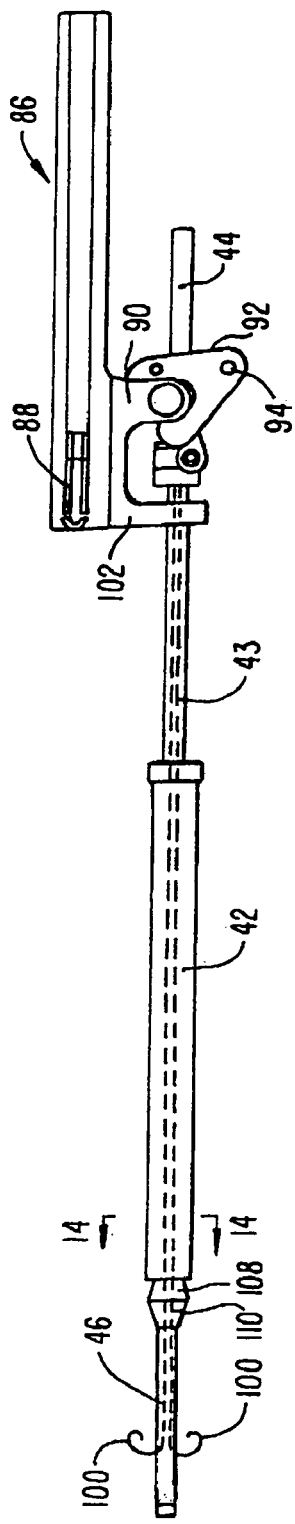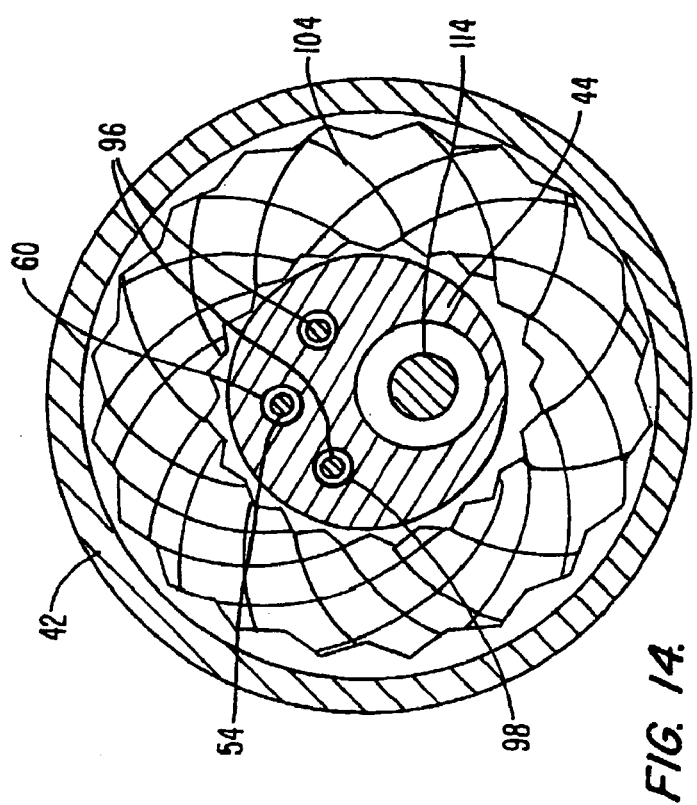

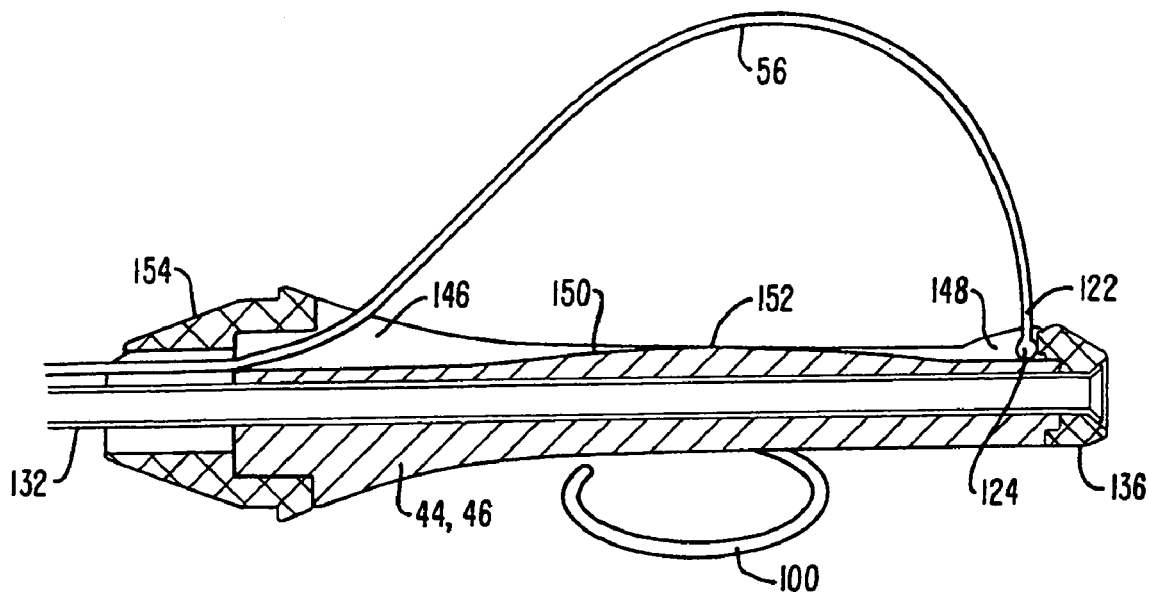
FIG. 27A
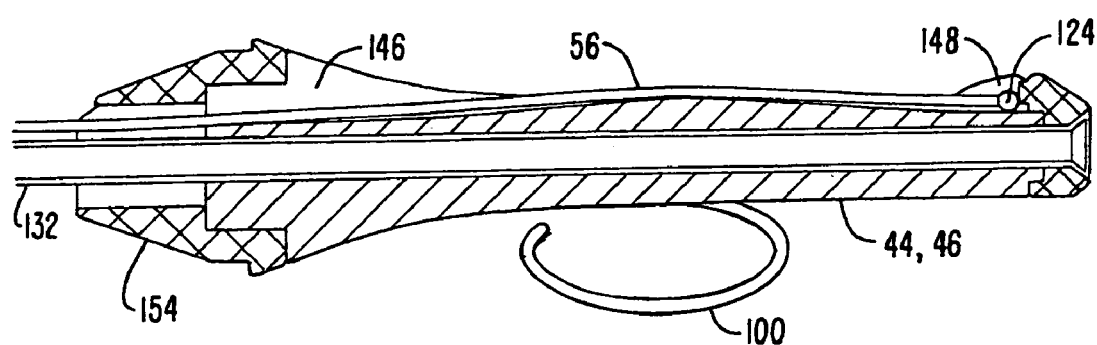
FIG. 27
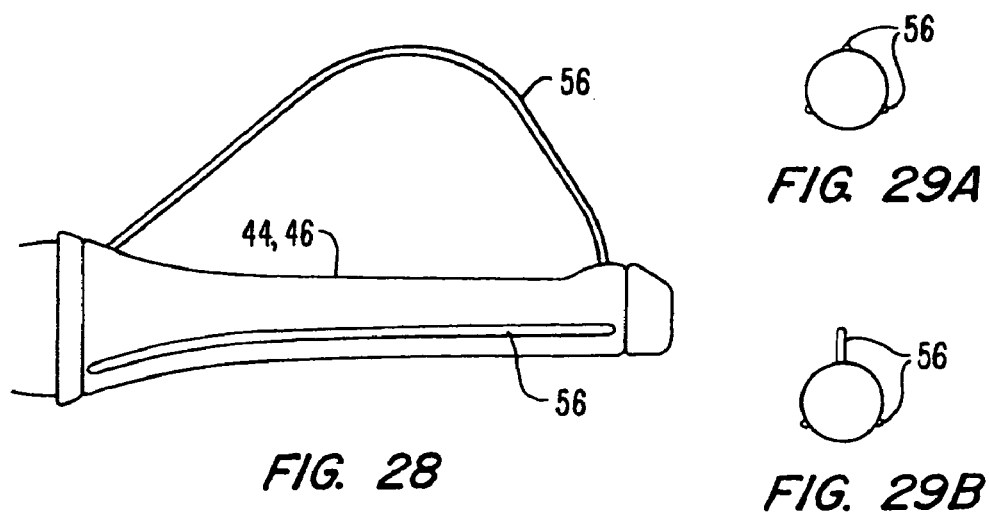
FIG. 28
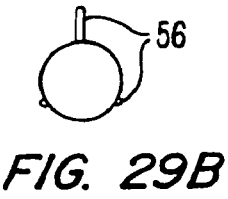
FIG. 29A
FIG. 29B

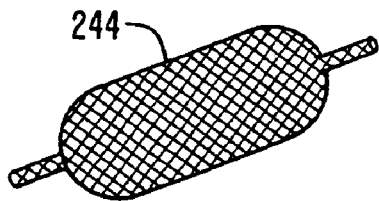
FIG. 40
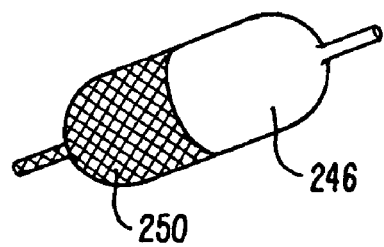
FIG. 41
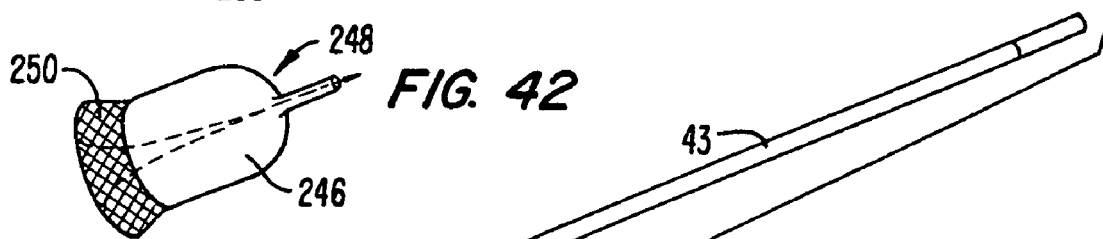
FIG. 42
FIG. 43
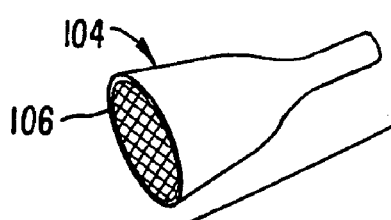
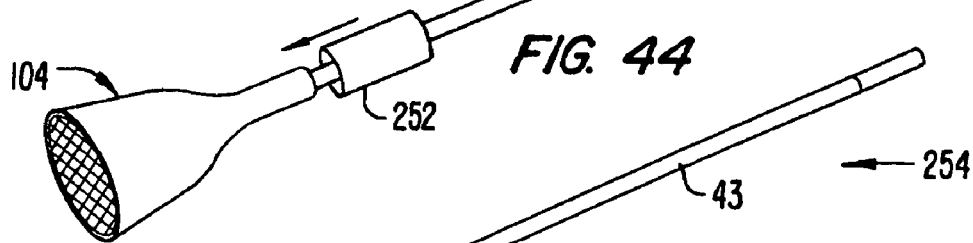
FIG. 44
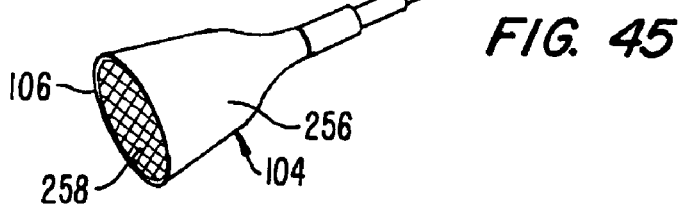
FIG. 45

TISSUE LOCALIZING AND SEPARATING ASSEMBLY

CROSS REFERENCE TO OTHER APPLICATIONS

This application is a continuation of U.S. patent application Ser. No. 10/374,583, filed Feb. 25, 2003, which is now U.S. Pat. No. 6,994,677, the entirety of which is hereby incorporated by reference.

This application is related to U.S. patent application Ser. No. 10/045,657 filed 7 Nov. 2001 and entitled Tissue Separator Assembly And Method, which is abandoned. This application is also related to U.S. patent application Ser. No. 10/374,582, filed Feb. 25, 2003, entitled Tissue Separating Catheter Assembly And Method, which is currently pending and U.S. patent application Ser. No. 10/374,584, filed Feb. 25, 2003, entitled Tissue Separating And Localizing Catheter Assembly, which is abandoned. See also: (1) U.S. Pat. No. 6,179,860 issued 30 Jan. 2001 and entitled Target Tissue Localization Device And Method, (2) International Publication No. WO 00/10471 published 2 Mar. 2000 and entitled Target Tissue Localization Device And Method, (3) U.S. Pat. No. 6,221,006 issued 24 Apr. 2001 and entitled Entrapping Apparatus And Method For Use, (4) International Publication No. WO 99/39648 published 12 Aug. 1999 and entitled Entrapping Apparatus And Method For Use, (5) U.S. patent application Ser. No. 09/588,278 filed 5 Jun. 2000 and entitled Tissue Removal Methods And Apparatus, which is now U.S. Pat. No. 6,530,923, (6) International Publication No. WO 00/74561 published 14 Dec. 2000 and entitled Tissue Removal Methods And Apparatus, and (7) U.S. patent application Ser. No. 09/844,661 filed 27 Apr. 2001 and entitled Intraoperative Tissue Treatment Methods, which is now U.S. Pat. No. 6,602,204.

BACKGROUND OF THE INVENTION

Cancer presently results in over one thousand five hundred deaths every day in the United States (550,000 deaths every year). Therapy modalities for cancer are plentiful and continued to be researched with vigor. Still, the preferred treatment continues to be physical removal of the cancer. When applicable, surgical removal is preferred (breast, colon, brain, lung, kidney, etc.). Open, excisional, surgical removal is often extremely invasive so that efforts to remove cancerous tissue in less invasive ways continue, but have not yet been perfected.

The only cure for cancer continues to be the early diagnosis and subsequent early treatment. As cancer therapies continue at earlier stages of diagnosis, the cancerous tissue being operated on is also smaller. Early removal of the smaller cancers demand new techniques for removal and obliteration of these less invasive cancers.

There is a variety of techniques that attempt to accomplish less invasive cancer therapy, but so far without sufficiently improved results. For example, the ABBI system from U.S. Surgical Corporation and the Site Select system from ImaGyn Corporation, attempt to accomplish less invasive cancer therapy. However, conventional techniques, in contrast with Minimally Invasive Surgery (MIS) techniques, require a large core (that is more than about 15 mm diameter) incision. Additionally, the Mammotome system from Johnson and Johnson and MIBB system from U.S. Surgical Corporation also require large core (over about 4 mm diameter) access to accomplish biopsy.

A convention held by the American Society of Surgical Oncologists on Mar. 13, 2000 reported that conventional stereotactic core biopsy (SCB) procedures fall short in providing definitive answers to detail precise surgical regimens after this SCB type vacuum assisted biopsy, especially with ductile carcinoma in situ (DCIS). Apparently these percutaneous systems damage "normal" tissue cells so that it is difficult to determine if the cells are "normal damaged" cells or early pre-cancerous (e.g. Atypical Ductal Hyerplasia (ADH)) cells.

A study presented by Dr. Ollila et al. from the University of North Carolina, Chapel Hill, demonstrated that histology and pathology is compromised using these conventional techniques because of the damage done to the removed tissue specimens. Hence, for many reasons, including the fact that DCIS is becoming more detectable and hence more prevalent in breast cancer diagnosis in the U.S., there is a growing need to improve upon conventional vacuum assisted core biopsy systems.

SUMMARY OF THE INVENTION

A first aspect of the invention is directed to a tissue localizing and separating assembly comprising a tissue separator assembly, an elongate coupler and a tissue localization assembly. The tissue separator assembly comprises a shaft and a tissue separator device with a distal separator part movable between retracted and operational states. The elongate coupler extends through the shaft and has a distal coupler end. The tissue localization assembly has a radially-expandable localization device at its distal end. The distal end of the coupler and the proximal end of the localization assembly may be joined together and moved into the catheter assembly thereby docking the tissue localization assembly to the tissue separator assembly.

A second aspect of the invention is directed to a method for docking a tissue separator assembly to a tissue localization assembly. A localization device of a tissue localization assembly is directed along a tissue track to a position at a target site. The localization device is changed to a radially-expanded state. A distal end of an elongated coupler is joined to the proximal end of the tissue localization assembly, the coupler passing through a catheter assembly of a tissue separator assembly. The joined proximal and distal ends are moved into the catheter assembly thereby docking the tissue localization assembly and the tissue separator assembly.

A third aspect of the invention is directed to a tissue-surrounding assembly comprising an elongate actuator element having a distal end and a tubular braided element. The tubular braided element comprises a body having a first end, mounted to the distal end of the elongate actuator element, and an open second end. The body is a radially expandable and contractible body having a trumpet-shape when in a relaxed state. The second end flares outwardly when the body is in the relaxed state.

A fourth aspect of the invention is directed to a method for making a tissue-surrounding assembly. A tubular braided element, having first and second end portions, is selected. A section of the tubular braided element is radially expanded, such as over a mandrel. A flexible material is applied to the first end portion, including a part of the radially expanded section, of the expanded tubular braided element. The flexible material may be applied by dipping the first end portion into a liquid material, with the tubular braided element on the mandrel, and then curing the liquid material to create the flexible material. The second end portion is directed into the first end portion to create a multi-wall tubular braided element with an inner end and an open outer end. The inner end is secured to an elongate actuator element.

A fifth aspect of the invention is directed to a tissue-penetrating assembly comprising a tissue-penetrating subassembly comprising a support assembly and a tissue-penetrating device, typically a needle, mounted to and extending from the support assembly. The tissue-penetrating device comprises a tissue-separating surface, typically the tip of the needle. The tissue-penetrating assembly also comprises a tissue-energizing circuit comprising an energy source and a force-sensitive switch selectively coupling the tissue separating surface to the energy source. The force-sensitive switch is operably coupled to the tissue-penetrating subassembly so that when a driving force applied to the tissue-penetrating device exceeds a level, the switch closes permitting energy from the energy source to reach the tissue separating surface, thereby aiding passage of the tissue-penetrating device through the tissue.

Other features and advantages of the invention will appear from the following description in which the preferred embodiments have been set forth in detail in conjunction with the accompanying drawings.

BRIEF DESCRIPTION OF THE DRAWINGS

FIG. 1 is a partially schematic overall view of a tissue separator assembly made according to the invention with portions of the handle removed for clarity;

FIG. 1A is a simplified cross-sectional view taken along line 1A-1A of FIG. 1 showing the engagement of a pin within a slot in the lead nut mounted to the lead screw;

FIGS. 5 and 6 show the handle and catheter assembly of FIG. 1 after the actuator has moved from the position of FIG. 1 and the actuator extension has pushed the separator wire pusher screw in a distal direction causing the separator wire to move radially outwardly;

FIG. 7 is a simplified the end view of the block and the pusher screw just after the pusher screw has exited the slot in the block showing the off-vertical orientation of the pusher screw;

FIG. 8 illustrates the proximal end of the lead screw, which is visible from outside the housing, and a rotary position indicator marked thereon corresponding to the position of the separator wire in FIG. 10;

FIGS. 9 and 10 illustrate the structure of FIGS. 5 and 6 after the drive screw has moved the actuator distally causing the lead nut to rotate the lead screw, catheter shaft and separator wire therewith about 540 degrees to create a separated tissue section;

FIG. 13 is a simplified view of certain of the components of FIG. 12;

FIG. 14 is a cross-sectional view of the catheter taken along line 14-14 of FIG. 13;

FIG. 27 is a somewhat simplified cross-sectional view of the structure of FIG. 25 with the separator wire portion in a radially retracted state;

FIG. 27A is a somewhat simplified cross-sectional view of the structure of FIG. 25 with the separator wire portion in a radially extended state;

FIG. 28 illustrates a further embodiment of the invention of FIG. 18 including three separator wire portions, one of which is shown in the operational state; and FIG. 29A is a simplified end view of the structure of FIG. 28 suggesting three equally-spaced separator wire portions, each in their retracted states;

FIG. 29B is a view similar to FIG. 29A but with one separator wire portion in an operational state;

FIG. 40 illustrates the shape of a tubular braided material after it has been stretched over a cylindrical mandrel having an enlarged central portion;

FIG. 41 illustrates the structure of FIG. 40 after one end of the mandrel and the tubular braided material has been dipped into a silicone compound;

FIG. 42 illustrates the open mesh end of the dipped tubular braided material, after the silicone has been cured and removed from the mandrel, being pulled back into the dipped end to create a tubular braided element;

FIG. 43 illustrates the resulting tubular braided element being mounted to the distal end of the actuator tube;

FIG. 44 shows the proximal end of the tubular braided element being secured to the distal end of the actuator tube by a length of heat shrink tubing; and FIG. 45 illustrates the tubular braided element secured to the actuator tube.

DESCRIPTION OF THE SPECIFIC EMBODIMENTS

Figure 2:
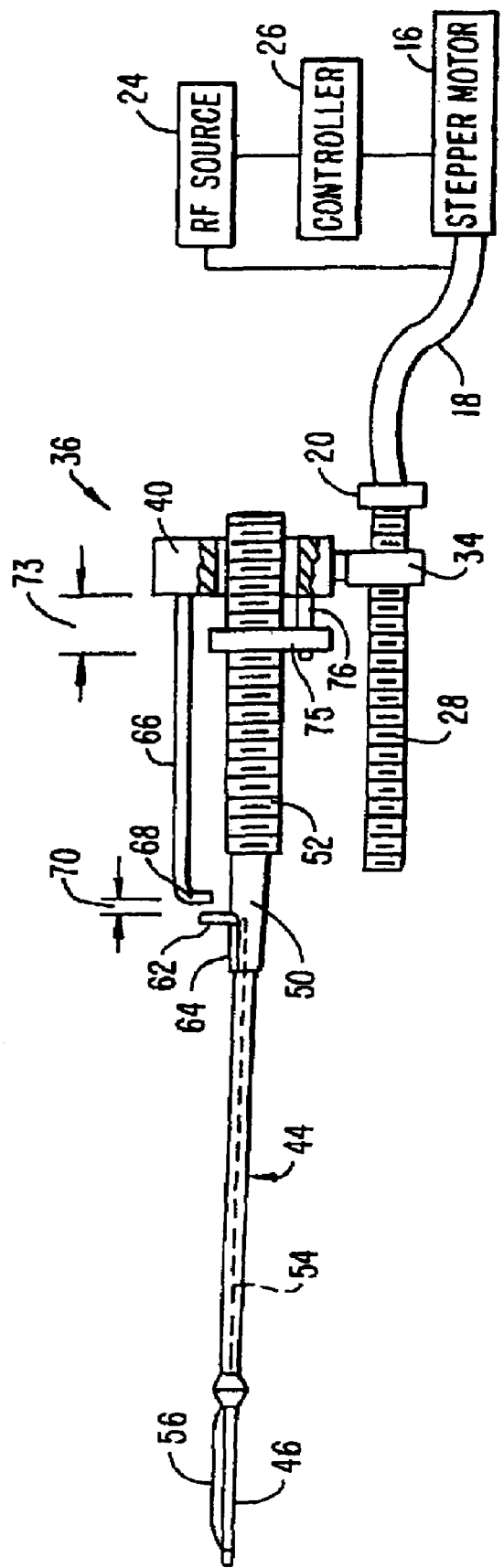
FIG. 2 is schematic view of portions of the drive elements of the assembly of FIG. 1.

FIGS. 1 and 2 illustrate a tissue separator assembly 10 used to separate target tissue from surrounding tissue, typically within a patient's breast. The removal of target tissue may be for diagnostic or therapeutic purposes. The assembly 10 includes a catheter assembly 12 extending from a handle 14. Introduction of catheter assembly 12 into the patient, typically through the skin, is preferably aided by the use of, for example, a trocar or an RF tip to provide a suitable path through the tissue. A stepper motor 16 is connected to handle 14 by a drive cable 18 and a drive cable connector 20 mounted to the handle housing 22. Note that in the Figs. only one-half of handle housing 22 is shown; the other housing half is substantially similar. RF energy is supplied to catheter assembly 12 from an RF source 24, along drive cable 18 and to the interior of handle 14. A controller 26 controls the operation of stepper motor 16 as well as RF source 24, such as speed of operation and energy level. Controller 26 also receives appropriate feedback signals from handle 14 and catheter assembly 12, such as tissue temperature, resistance force. signals, tissue impedance, rotary orientation, and so forth.

Figure 4:
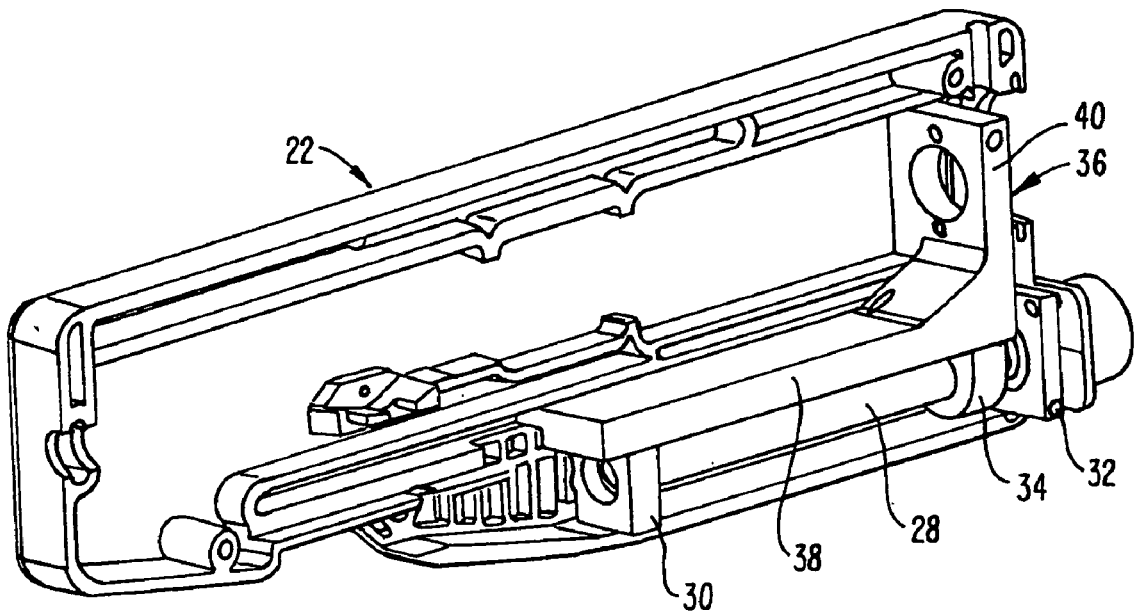
FIG. 4 is an oblique view of the housing half of FIG. 1 together with the drive screw, drive nut and an L-shaped actuator connected to and movable with the drive nut.

Drive cable 18 is connected to and rotates a drive screw 28 rotatably mounted within handle 14 at a fixed axial location by drive screw supports 30, 32. A drive nut 34 is threadably mounted to drive screw 28. An L-shaped actuator 36 is secured to drive nut 34. Actuator 36, see FIG. 4, includes a generally horizontal base portion 38 and a generally vertical upright portion 40 sized and configured to move within handle 14 parallel to the axis of drive screw 28. Therefore, rotation of drive screw 28 by stepper motor 16 causes actuator 36 to slide within housing 22 from the initial position of FIG. 1 to the position of FIG. 10. Reverse and reciprocating movement is also possible.

Catheter assembly 12 includes in introducer sheath 42 mounted to and extending from housing 22. Catheter assembly 12 also includes an actuator tube 43, discussed below with reference to FIGS. 14-17, passing through sheath 42 and a shaft 44 passing through tube 43. See FIG. 3. Shaft 44 has a distal portion 46 extending distally of the distal end 48 of sheath 42 and a proximal portion 50 extending into the interior of handle 14. Proximal portion 50 is secured to and rotates with a lead screw 52. Accordingly, shaft 44 rotates with lead screw 52. Lead screw 52 is mounted within housing 22 in a manner so that it can rotate but not move axially within housing 22. A tissue separator device 54 extends along shaft 44 and has a separator wire portion 56 secured to the distal end 58 of shaft 44. The separator wire 56 is positioned externally of distal portion 46. The majority of tissue separator device 54 is in the form of a wire and extends through an axial bore 60 formed in shaft 44. The separator device 54 has a radially extending pusher screw 62 at its proximal end. The proximal end of shaft 44 has an axially extending slot 64, see FIG. 2, through which pusher screw 62 extends. Accordingly, pushing pusher screw 62 distally, that is to the left in the FIGS., causes tissue separator wire 56 to move outwardly from its radially contracted condition of FIG. 1 to its radially extended condition of FIGS. 5 and 6. This radially outwardly movement is typically accomplished at the target site within the patient, typically a patient's breast. To aid movement of separator wire through the tissue, wire 56 is supplied with RF energy from RF source 24. Other applications of energy, such as mechanical reciprocation or mechanical vibration, can also be used.

The axial movement of pusher screw 62 is caused by the axial movement of actuator 36. Actuator 36 has an extension 66 extending distally from upright portion 40. Extension 66 has a downwardly formed distal end 68 aligned with pusher screw 62. The initial axial movement of actuator 40, caused by the rotation of drive screw 28 by stepper motor 16, closes a small gap 70 (see FIG. 2) between distal end 68 and pusher screw 62. This small gap permits the initiation of an electrosurgical arc prior to the outwardly radial movement of separator wire 56. Continued distal movement of actuator 36 moves pusher screw 62 distally causing separator wire 56 to bow outwardly to the position of FIGS. 5 and 6. FIGS. 5 and 6 (but not FIG. 1) show the use of a support block 72, which is a part of housing 22, to support the distal end of lead screw 52 and the proximal end of shaft 44. Support block 72 has an axially extending slot 74, see FIGS. 5 and 7, which initially houses pusher screw 62. At the time separator wire 56 is fully extended, pusher screw 62 exits slot 74 and the distal end 68 of extension 66, which has a chamfered face, causes pusher screw 62, along with shaft 44, to begin rotating to the off-vertical position of FIG. 7. At the same time upright portion 40 of actuator 36 closes gap 73 (see FIG. 2) and contacts a lead nut 75 threadably mounted on lead screw 52. An anti-rotation pin 76 extends from upright portion 40 of actuator 36 and is housed within a U-shaped slot 78 formed in lead nut 74, see FIG. 1A, to prevent lead nut 74 from rotating around lead screw 52 as lead nut 74 it is moved axially by actuator 36. Instead, the axial movement of actuator 36 causes lead screw 52 to rotate thus rotating shaft 44. Assembly 10 is configured so that shaft 44 rotates about 540 degrees to ensure a tissue section 80 is completely separated from the surrounding tissue by the passage of separator wire 56 through the tissue. The radial position of separator wire 56 can be easily determined by looking at the proximal end 82 of lead screw 52, which is exposed through housing 22. See FIG. 8. Proximal end 82 has a rotary position indicator 84 formed thereon corresponding to the rotary position of separator wire 56.

The above-described sequence of events, according to this disclosed embodiment, proceeds automatically once initiated by a user. Of course operation of the device, including one or more of extension of separator wire 56, rotation of shaft 44 and energizing wire 56, can be terminated manually or automatically based on, for example, an unexpected resistance to the rotation of shaft 44.

Figure 3:
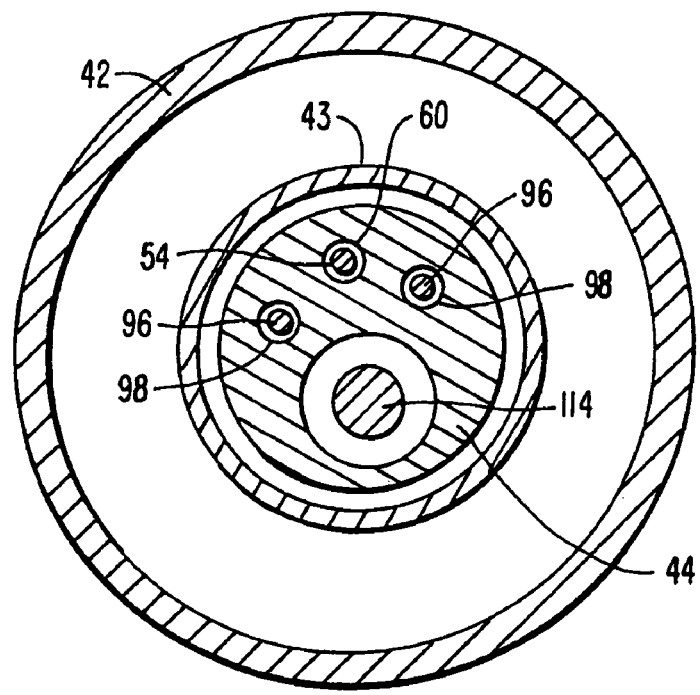
FIG. 3 is a simplified cross-sectional view of the catheter assembly taken along line 3-3 of FIG. 1.
Figure 11:
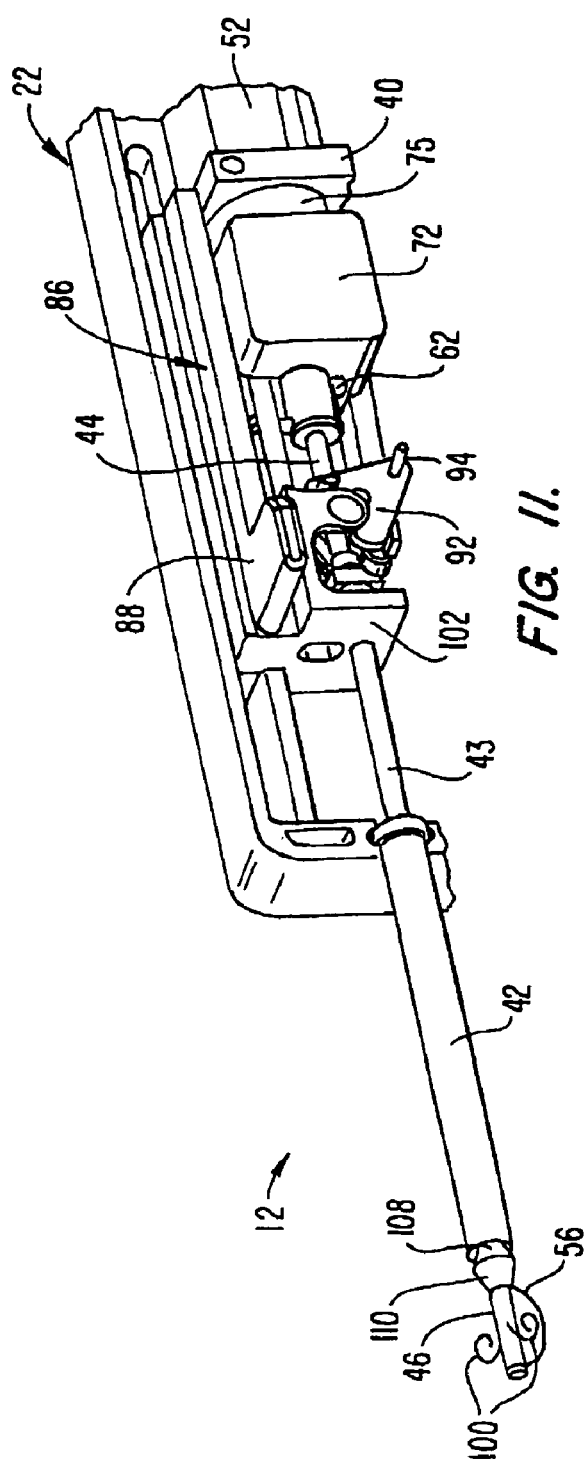
FIGS. 11 and 12 illustrate the manual actuation of tissue section holding elements.
Figure 12:
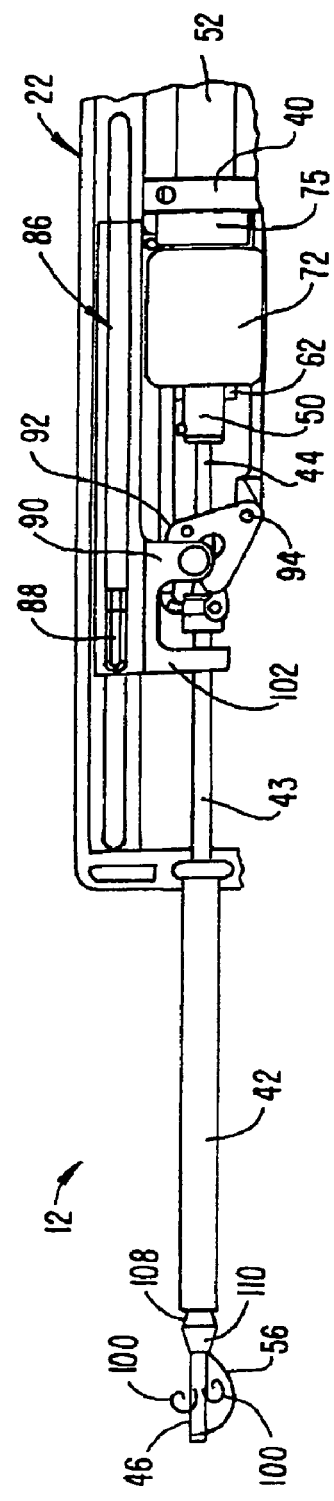
Figure 15:
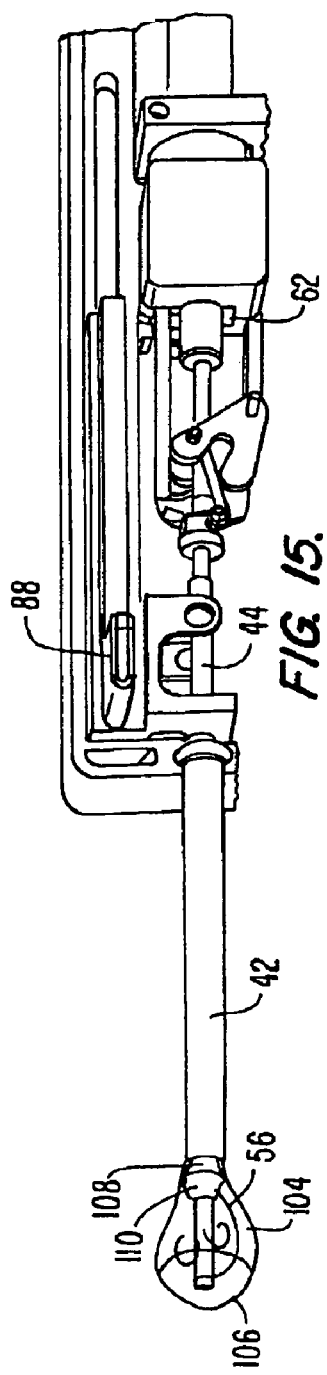
FIGS. 15 and 16 illustrate the manual actuation of a tubular braided element to surround the separated tissue section.
Figure 16:
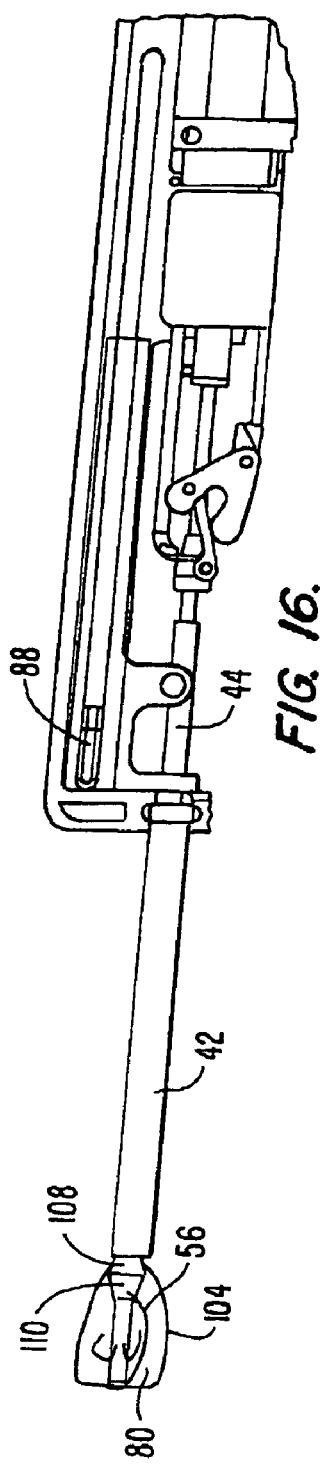
Figure 17:
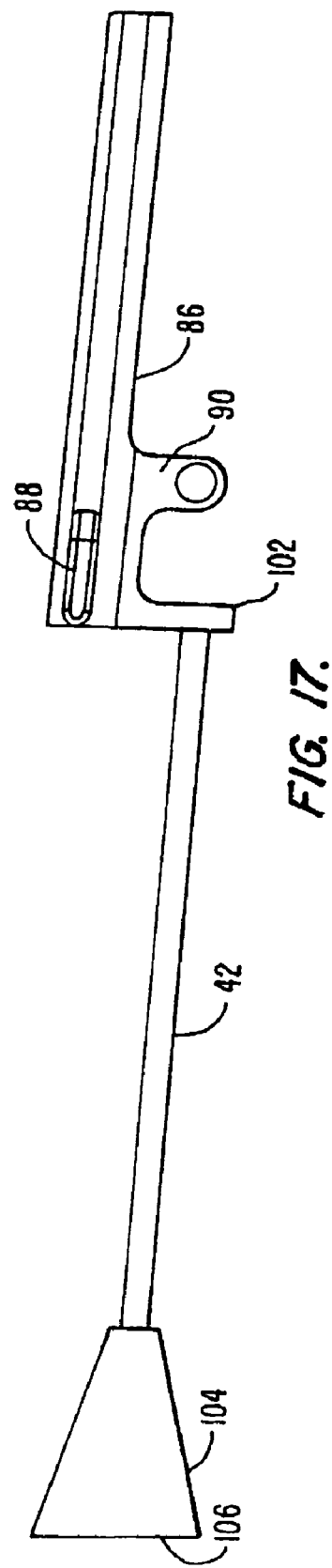
FIG. 17 is a simplified view of certain of the components of FIG. 16.

Assembly 10 also includes a T-pusher device 86 having a pair of pusher tabs 88 extending laterally outwardly from slots formed in housing 22. See FIGS. 11-13. After shaft 44 has completed its rotation, the user begins pushing tabs 88 distally. This causes an extension 90 of device 86 to rotate a flipper cam 92 about a pivot pin 94; flipper cam 92 is connected to the proximal ends of a pair of tissue section holding elements 96. Holding elements 96 are in the form of wires passing through axial bores 98 formed in shaft 44 as shown in FIG. 3. The distal ends of holding elements 96 are preformed hook wires 100, preferably made of a shape memory material such as Nitinol, which pass through openings formed in distal portion 46 of shaft 44 and engage separated tissue section 80 to help secure tissue section 80 to distal portion 46 of shaft 44.

Device 86 includes a distal end 102 connected to the proximal end of actuator tube 43. Thus, the movement of device 86 causes tube 43 to move distally within introducer sheath 42. At this point, that is with hook wires 100 deployed as an FIGS. 11-13, a tubular braided element 104, see FIGS. 14-17, secured to the distal end of actuator tube 43, is still fully housed within sheath 42. Further distal movement of device 86 causes tubular braided element 104 to extend outwardly past distal end 48 of sheath 42 to the position of FIGS. 15-17. The purpose of tubular braided element 104 is to surround separated tissue section 80 by passing along the dissection plane between the separated tissue section and the surrounding tissue. The open outer end 106 of element 104 naturally expands radially as it is pushed axially through the tissue. To aid the proper initial radial expansion of element 104, shaft 44 has an outwardly tapered guide surface 108, formed on a guide element 110, positioned adjacent to distal end 48 of introducer shaft 42. The proper radial expansion of element 104 may also be aided by the shape that element 104 takes when in its relaxed state. See, for example, the discussion of tubular braided element 104 with regard to FIGS. 40-45. Guide element 110 has a slot in its proximal surface into which the proximal end of separator wire 56 passes when in the radially expanded condition of FIG. 9; this helps to keep separator wire 56 from folding over during rotation. If desired, outer end 106 of tubular braided element 104 could include a drawstring or other type of closure element. The separated tissue section 80, now substantially enclosed within tubular braided element 104 and secured to distal portion 46 of shaft 44 by hook wires 100, may be removed from the patient.

With the present invention separated tissue section 80 retains most if not all of its physical integrity once removed from the patient. Also, the use of tubular braided element 104, especially when it is sealed or otherwise impermeable to the passage of material, helps to reduce the possibility of seeding diseased tissue along the tissue track during removal of separated tissue section 80.

Figure 18:
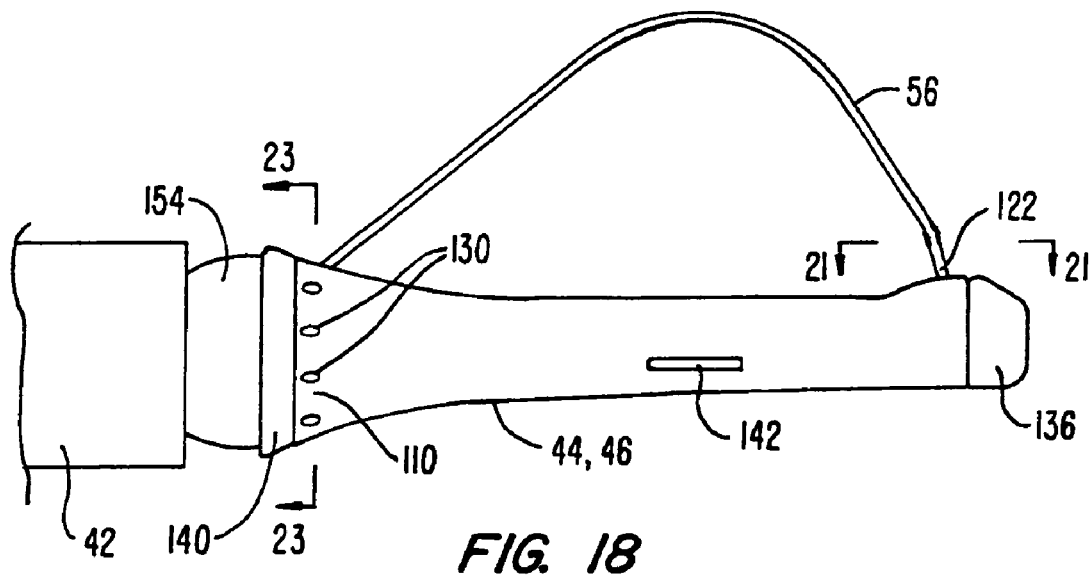
FIG. 18 is enlarged side view of the distal end of an alternative embodiment of the catheter assembly of FIG. 1.
Figure 19:
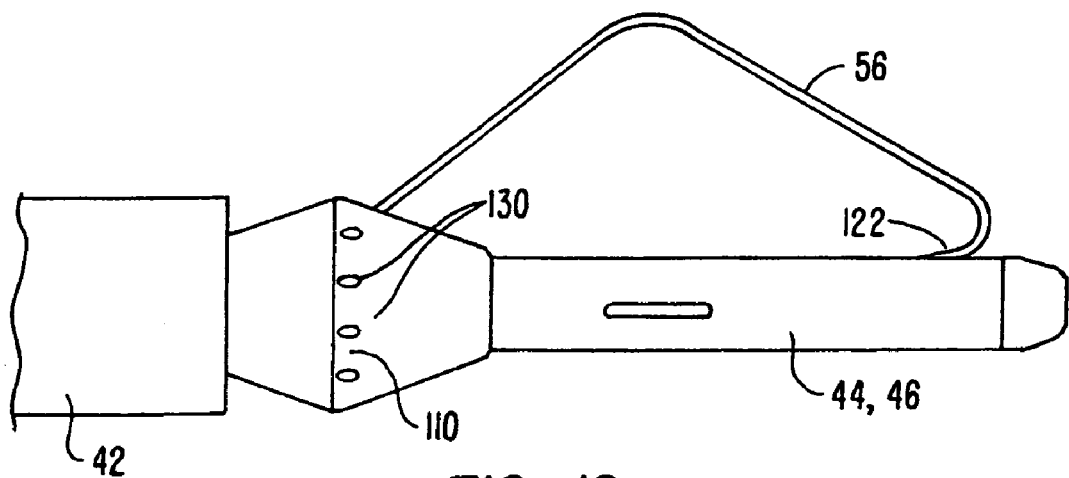
FIG. 19 is a side view of a modified embodiment of the distal end of the catheter assembly of FIG. 18.
Figure 20:
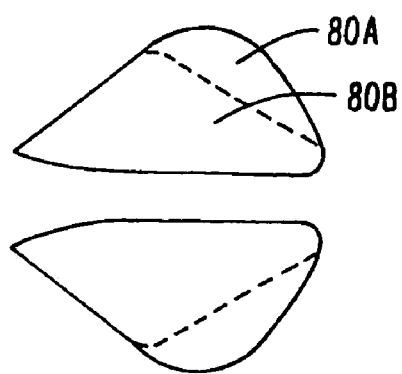
FIG. 20 is a schematic illustration showing the difference in size between the separated tissue sections of the embodiments of FIGS. 18 and 19.
Figure 22:
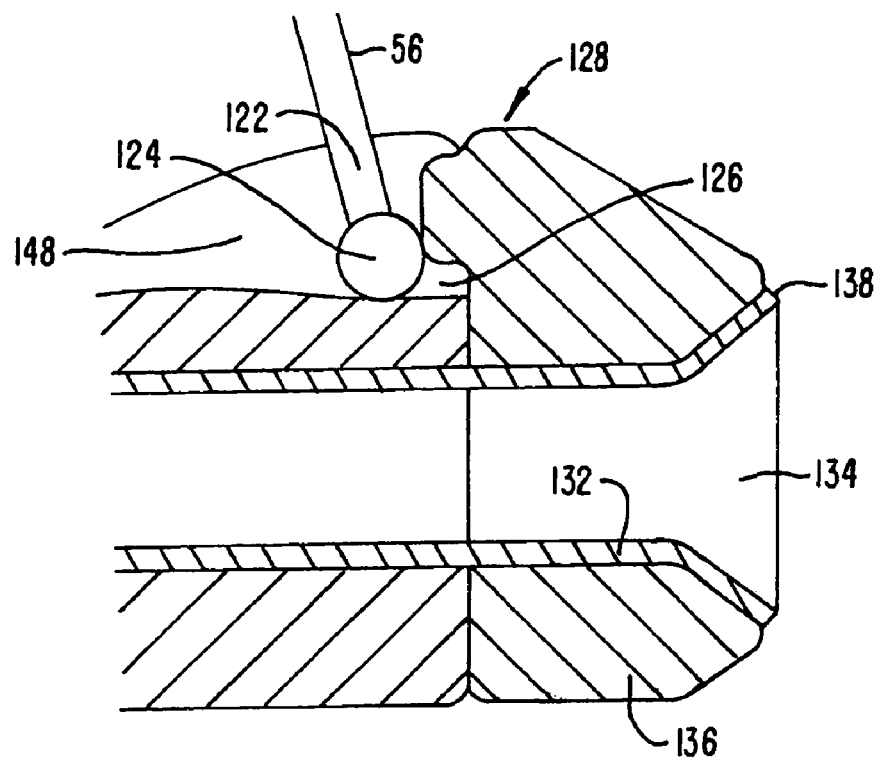
FIG. 22 is an enlarged cross-sectional view taken along the line 22-22 of FIG. 21.
Figure 21:
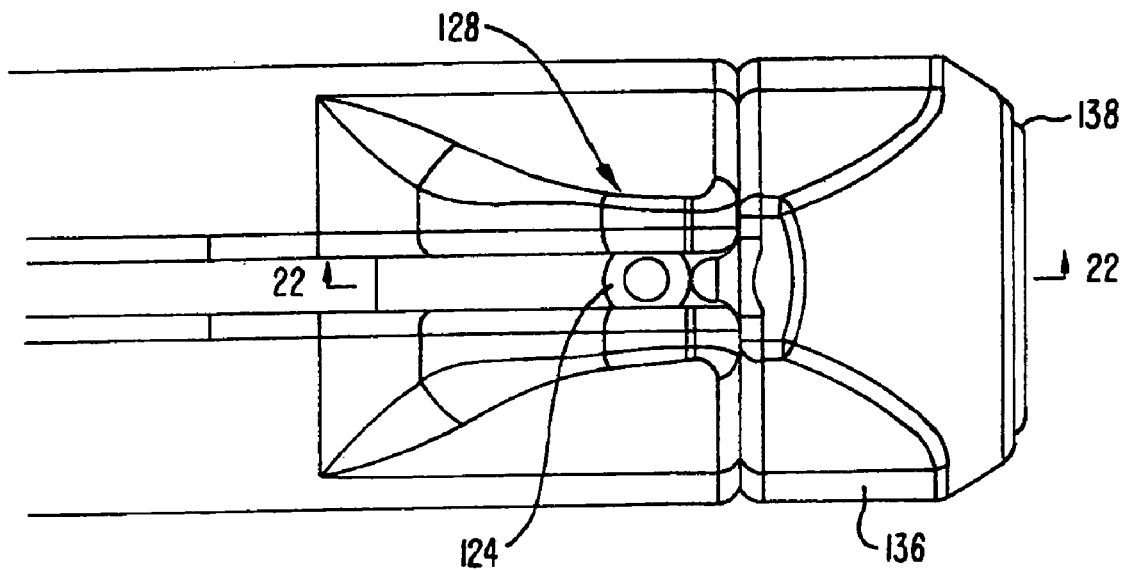
FIG. 21 is an enlarged top view taken along line 21-21 of FIG. 18.

FIGS. 18-29B illustrate further embodiments of the invention with like reference numerals referring to like elements. FIG. 18 is an enlarged side view of the distal end 120 of alternative embodiment of the catheter assembly 12 of FIG. 1. Referring now also to FIGS. 21, 22 and 27, separator wire portion 56 is seen to include a distal end 122. Distal end 122 terminates at a ball-type element 124 (see FIG. 22) housed within a cavity 126 defined within distal portion 46 of shaft 44 at the tip 136 of the distal portion to form a pivot joint 128. The provision of pivot joint 128 permits distal end 122 to effectively pivot freely as separator wire portion 56 is moved between the operational and retracted states. In addition to reducing stresses and improving the fatigue characteristics of distal end 122 of separator wire portion 56, the use of pivot joint 128 helps to increase the volume of the separated tissue section removed from the patient for the same distance of travel of tissue separator device 54. This increase in volume may be appreciated by comparing the embodiments of FIGS. 18 and 19. In the FIG. 19 embodiment, the distal end 122 of separator wire portion 56 is rigidly or otherwise non-pivotally secured to distal portion 46 of shaft 44. FIG. 20 illustrates the increased volume of separated tissue section 80A resulting from the embodiment of FIG. 18 to the reduced volume, separated tissue section 80B from the embodiment of FIG. 19. In this example the volume of separated tissue section 80A has been calculated to be about 50 percent greater than the volume of separated tissue section 80B for the same distance of travel of tissue separator device 54.

Figure 23:
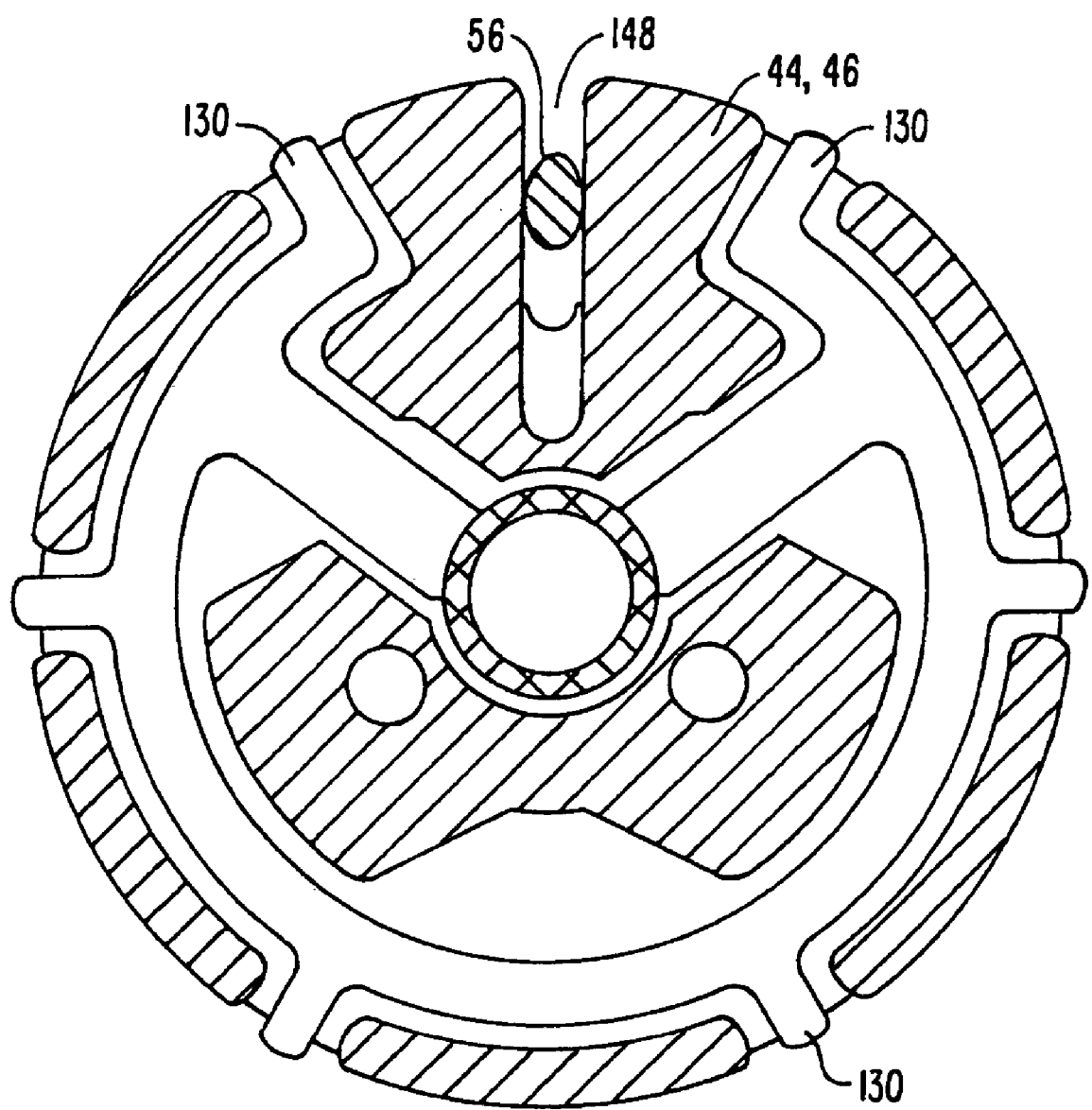
FIG. 23 is a cross-sectional view taken along line 23-23 of FIG. 18.

Distal portion 46 of shaft 44 includes guide element 110 which acts as a transition surface 110. Transition surface 110 is a distally-facing surface extending radially outwardly and proximally, that is longitudinally away from the tip 136 of distal portion 46. A series of spaced-apart, first, proximal energizable tissue separator elements 130 are positioned along transition surface 110. FIG. 23 is a cross-sectional view taken along line 23-23 of FIG. 18 and illustrates the electrical connection of elements 130 to metallic tube 132.

Figure 24A:
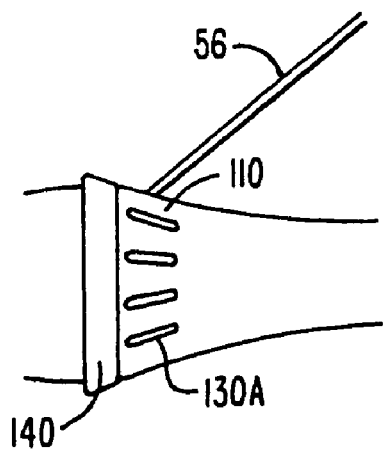
FIGS. 24A-24H are simplified side views of different embodiments of the guide element/transition surface of FIG. 18.
Figure 24B:
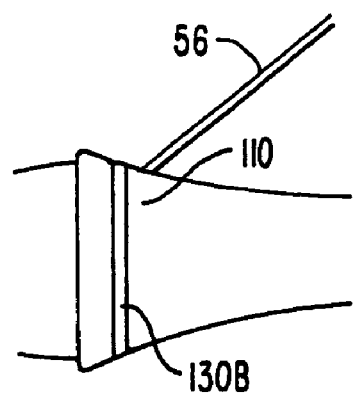
Figure 24C:
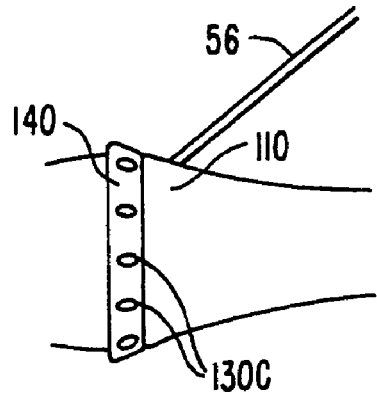
Figure 24D:
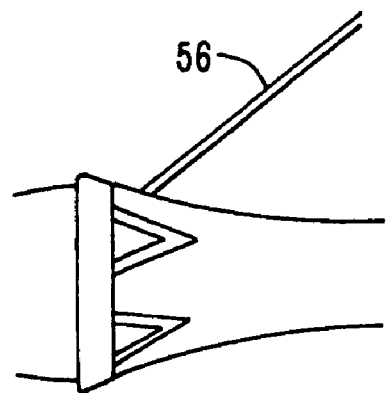
Figure 24E:
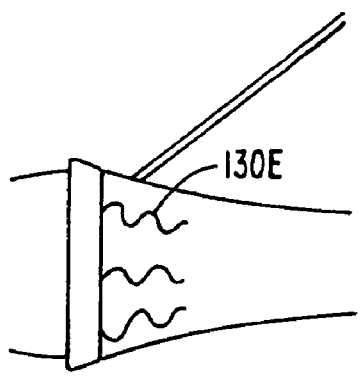
Figure 24H:
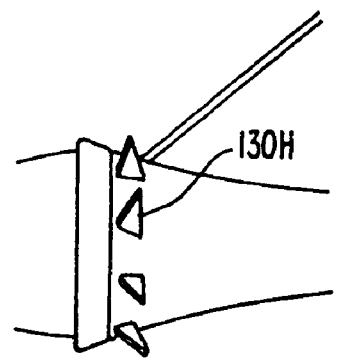
Figure 24F:
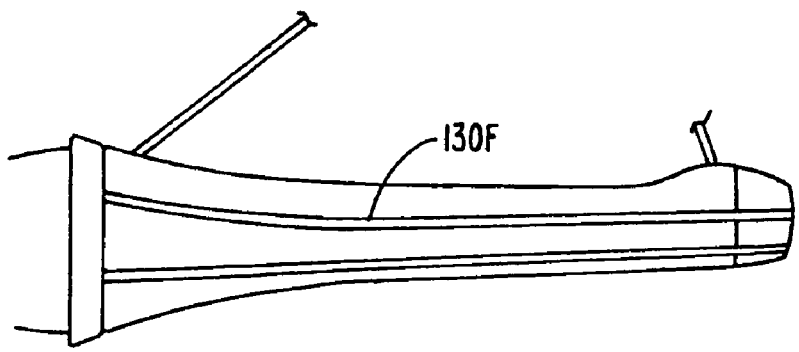
Figure 24G:
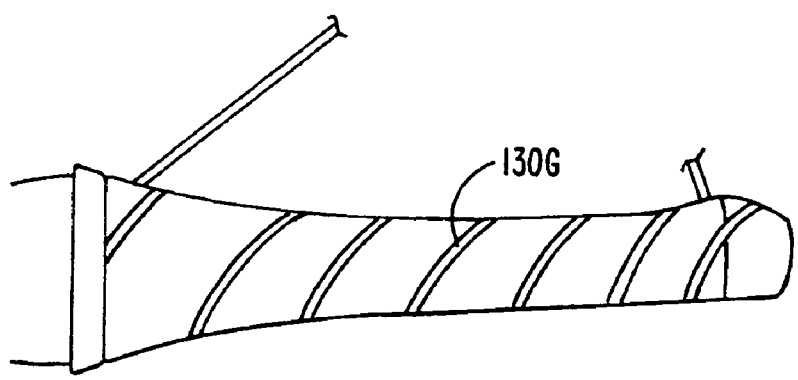

FIGS. 24A-24H illustrate alternative embodiments of first elements 130. Elements 130A have extended longitudinal lengths, as compared with the essentially circular elements 130 of FIGS. 18 and 23. It is believed that the extended lengths of element 130A may be useful for reducing the penetration force needed for placement at the target site. The FIG. 24A embodiment is the presently preferred embodiment. Element 130B comprises a circumferentially continuous or substantially circumferentially continuous element. The circumferentially extending element 130B may also be useful for reducing the required penetration force. Elements 130C are similar to elements 130 but are located at peripheral region 140 of transition surface 110. Elements 130D and 130E, shown in FIGS. 24D and 24E, are generally V-shaped and serpentine-shaped variations. Elements 130F and 130G, shown in FIGS. 24F and 24G, extend along substantially the entire lengths of distal portion 46 in straight and spiral configurations, respectively. FIG. 24H illustrates a further embodiment of elements 130H with elements 130H extending radially outwardly from distal portion 46; elements 130H may be retractable and may have shapes other than the pointed, triangular shape illustrated. While elements 130 are typically formed from metal wires or similar structure, elements 130 may also be painted, plated or otherwise deposited on the surface of distal portion 46. A combination of two or more of the arrangements of element 130 may be useful in appropriate circumstances. While presently all of elements 130 are supplied with equal energy levels, different energy levels may be supplied. Also, the energy levels supplied may be varied over time or according to the resistance to the passage of separator wire portion 56 through the tissue. Also, energy to elements 130 may be turned on as needed at the discretion of the user.

Distal portion 46 is hollow and contains an electrically conductive, metallic tube 132 defining an opening 134 at the tip 136 of distal portion 46. The outer, annular edge of tube 132 acts as a second, distal energizable tissue separator element 138. Both first element 130 and second element 138 are selectively coupleable to one or more appropriate energy sources to aid movement of distal portion 46 through tissue to the target site.

Figure 25:
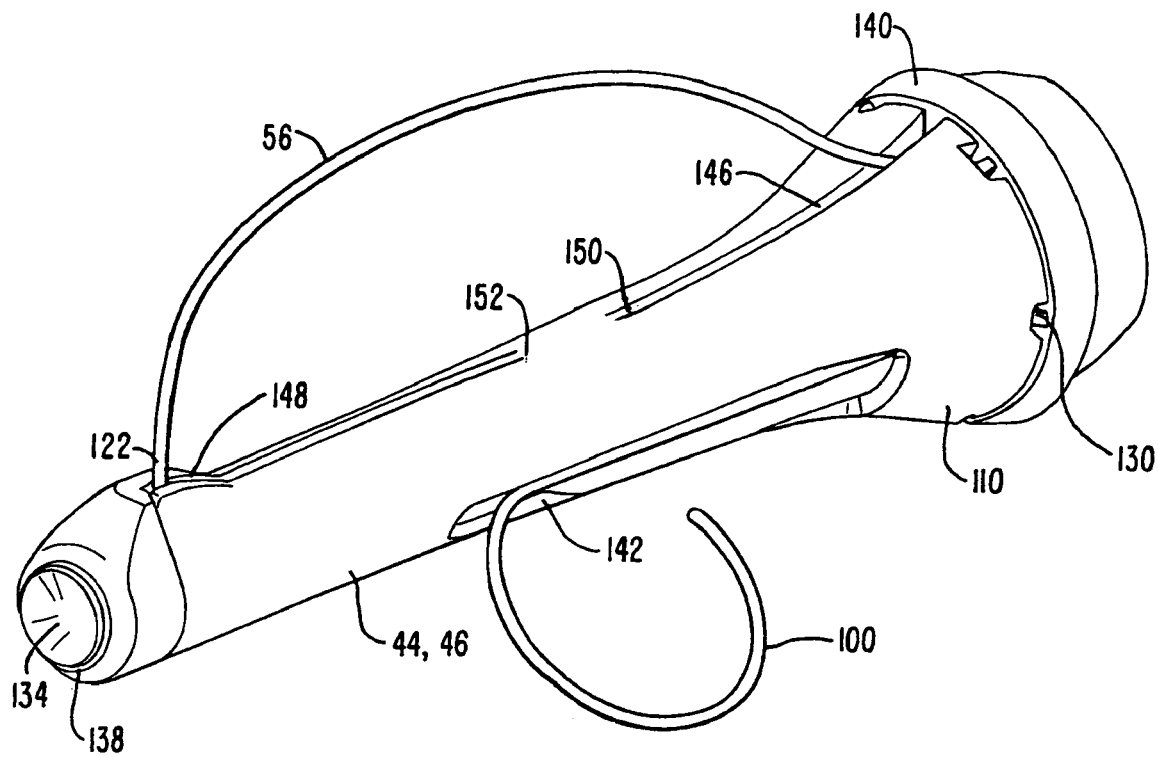
FIG. 25 is an overall view of the distal end of the catheter assembly of FIG. 18 illustrating a hook wire/tissue holding element in a deployed condition.
Figure 26:
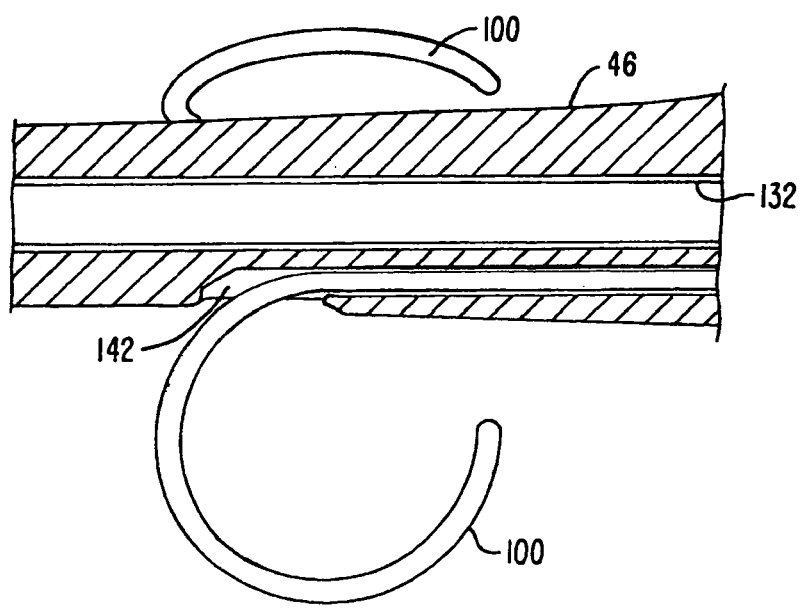
FIG. 26 is a cross-sectional view of a portion of the shaft of FIG. 25.

FIGS. 25 and 26 illustrate the hook wires 100, which act as tissue holding elements, extending through openings 142 formed within distal portion 46 of shaft 44. Hook wires 100 are preferably sized, positioned and shaped to engage separated tissue section 80 at about its center of mass. While two hook wires 100 are shown in this embodiment, a greater or lesser number may also be used. Also, hook wires 100 having different sizes and shapes may be used. Hook wires 100 may also be located at different axial positions and may be energizable to aid movement through tissue.

FIGS. 25, 27 and 27A illustrate the passage of separator wire portion 56 through proximal and distal channels 146, 148 formed in distal shaft portion 46. Distal portion 46 defines a base surface 150 extending along the bottoms of channels 146 and 148 and extending between channels 146 and 148. Separator wire portion 56 lies against base surface 150 when in a retracted state. As shown best in FIGS. 27 and 27A, the central portion 152 of base surface 150 is convex so that when separator wire portion 56 is in the retracted state, a central portion of wire portion 56 lies along a convex line, that is a line that bows slightly outwardly. Therefore when tissue separator device 54 is moved distally, separator wire portion 56 is predisposed to move radially outwardly in the desired manner. The amount of force needed to be applied to device 54 may also be reduced by the use of convex central portion 152.

FIG. 28 illustrates a further alternative embodiment to the embodiment of FIG. 18 comprising three separator wire portions 56, as opposed to one in FIG. 18, one wire portion 56 being shown in an operational state and the other two wire portions 56 in retracted states and adjacent base surfaces 150. This is suggested in FIG. 29B. Another difference from the embodiment of FIG. 18 is that the function of first, proximal energizable tissue separator elements 130 has been replaced by energizing the three separator wire portions 56 when the device is directed through tissue to a target site with wire portions 56 in retracted states. This is suggested in FIG. 29A. Once at the target site the physician may decide to move one, two or all three of separator wire portions 56 from the retracted state to the operational state depending on various factors, such as the characteristics of the tissue and the number of pieces tissue section 80 is to be divided into.

Distal portion 46, in the embodiment of FIGS. 18-29B, comprises a proximal element 154, a body portion 156 and tip 136, tip 136 acting as an end cap. FIG. 27 illustrates the interengagement of elements 154, 156 and 136. Elements 154, 156 and 136 are configured to promote simple assembly. Assembly may take place by simply stacking each element in order over central tube 132, the parts being held in place distally by the flared end 138 of the tube. Elements 154, 156 and 136 are preferably electrically non-conductive. Elements 154 and 156 are typically made from the medical grade ceramic material, such as $Al_2O_3$ or zirconia, while tip 136 is typically made from a medical grade polymer, such as PEEK or polyimide.

The amount of force required for the passage of a needle, or other tissue-penetrating element, such as distal portion 46 of shaft 44, through tissue often changes because the tissue characteristics often changes between the point of entry and the target site. If the tissue-penetrating element must pass through a hard or otherwise difficult-to-penetrate tissue region, the amount of force needed to penetrate the hard tissue region may be sufficiently great to, for example, cause the tissue-penetrating element to buckle. Even if the tissue-penetrating element has sufficient columnar strength to resist buckling, the amount of force required may be sufficient to cause the tissue to be deformed making it difficult to position the tip of the tissue-penetrating element at the target site. Also, once the tip has passed through the difficult-to-penetrate tissue region, the amount of force needed to do so may tend to cause the tip of the tissue-penetrating element to be inserted much farther than desired causing unintended tissue trauma and possibly injuring adjacent organs.

Figure 30:
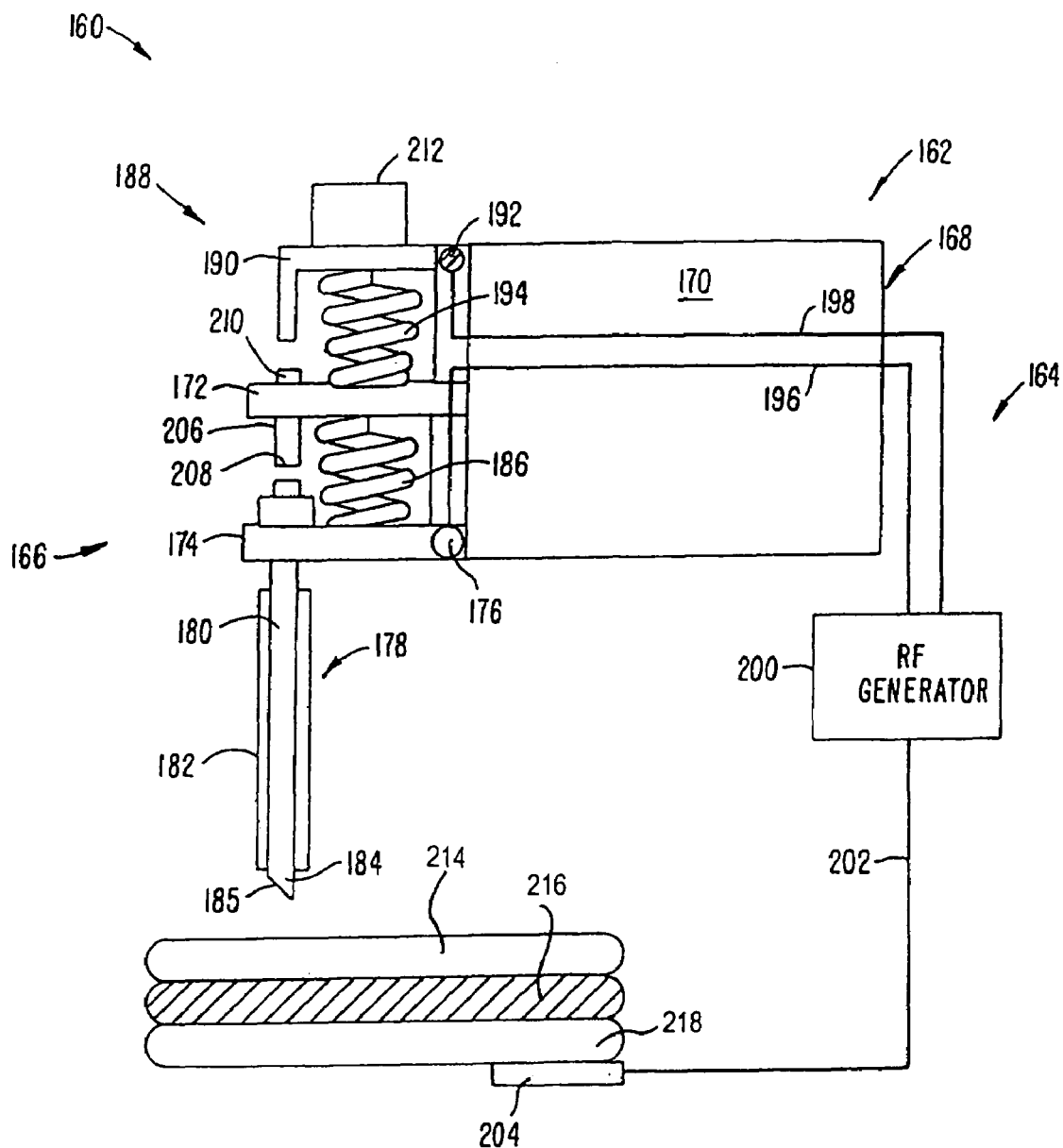
FIG. 30 is a simplified schematic illustration of a tissue-penetrating assembly.
Figure 31:
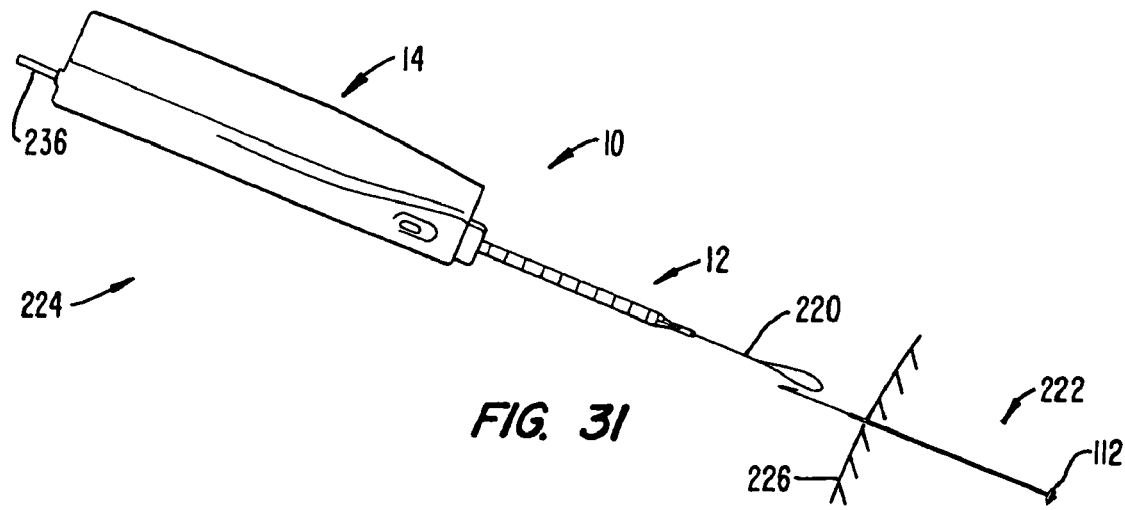
FIG. 31 is an overall view of a tissue localizing and separating assembly made according to the invention including a tissue separator assembly, a coupler and a tissue localization assembly, the localization device of the tissue localization assembly being in an expanded condition at a target site within a patient.
Figure 32:
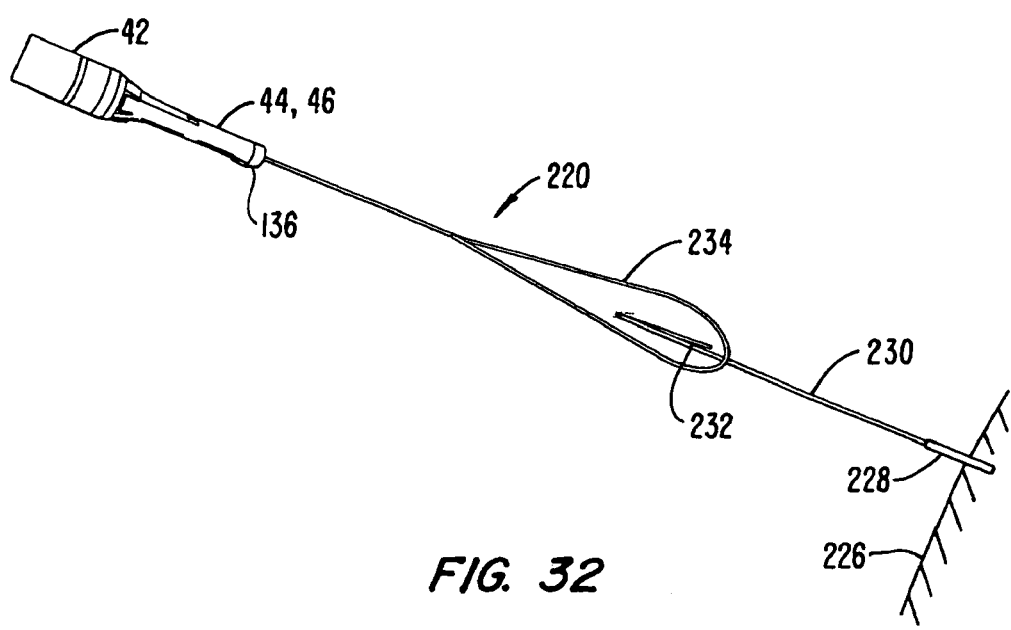
FIG. 32 is an enlarged view of a portion of the assembly of FIG. 31 illustrating a loop at the distal end of the coupler being engaged with the proximal end of the tissue localization assembly.
Figure 33:
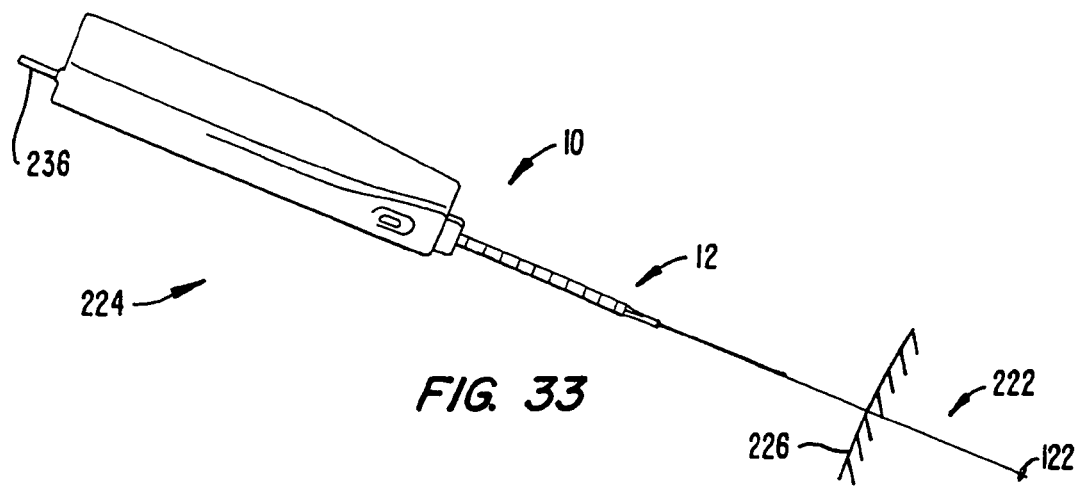
FIGS. 33 and 34 illustrate the distal end of the coupler and the proximal end of the tissue localization assembly of FIG. 31 joined to one another.

FIG. 30 illustrates, in schematic form, a tissue-penetrating assembly 160 comprising broadly a tissue-penetrating subassembly 162 coupled to a tissue-energizing circuit 164 and a force-sensitive switch 166 operably coupled to the tissue-penetrating subassembly. The subassembly 162 comprises a handle assembly 168, or other support assembly, including a handle 170, a handle extension 172 extending rigidly from handle 170, and a needle clamp 174 mounted to handle 170 at a pivot 176. Subassembly 162 also includes a needle 178, or other tissue-penetrating device, secured to and extending from needle clamp 174. Needle 178 includes a needle shaft 180 covered by electrical insulation 182 along most of its length. Electrical insulation 182 helps to concentrate the tissue-penetrating energy at the tip 184 of needle 178, tip 184 having a tissue-separating surface 185.

Force-sensitive switch 166 includes a compression spring 186 captured between needle clamp 174 and handle extension 172. Assembly 160 also includes an arming switch 188 mounted to handle 170, switch 188 including an arm 190 mounted to handle 170 at a pivot 192. Switch 188 also includes an arming compression spring 194 captured between arm 190 and handle extension 172. The use of arming switch 188 helps to enhance the safety of assembly 160 by helping to prevent the inadvertent connection of arm 190 to needle clamp 174, which would signal RF generator 200 to apply RF energy between RF signal 196 and return signal 202. Circuit 164 includes lead 196 electrically connected to needle clamp 174, and thus needle tip 184. Circuit 164 also connects signal 198 to arm 190 through pivots 176, 192, respectively. Circuit 164 also comprises an RF generator 200, from which leads 196, 198 extend, and a return cable 202 coupling generator 200 to a return pad 204. An electrical conductor 206 is mounted to handle extension 172 and has electrical contact surfaces 208, 210 positioned opposite the corresponding surfaces of needle shaft 180 and arm 190. An arming button 212 is mounted to arm 190 to permit the user to arm assembly 160 by pressing an arming button 212 to cause arm 190 to contact surface 210. With the device now armed, needle 178 is directed into tissue, exemplified by three layers of tissue, including soft tissue layers 214 and 218 and hard or otherwise difficult-to-penetrate tissue layer 216. Upon encountering hard tissue layer 216, the force needed to penetrate tissue layer 216 is sufficient to compress spring 186 and cause needle shaft 180 to contact electrical contact surface 208 thus completing the circuit between signal 196 and signal 198 of RF generator 200. RF generator 200 will then supply energy to surface 185 at tip 184 permitting needle 178 to pass through hard tissue 216 without excessive force. Once tip 184 has passed through hard tissue layer 216, the force on needle 178 decreases to permit spring 186 to separate needle shaft 180 from contact surface 208 so to stop supplying RF energy to tissue separator surface 185.

Tissue-penetrating assembly 160 can be used to aid the insertion of a simple needle into tissue. However, the tissue-penetrating invention also can be incorporated into other devices including tissue-penetrating elements, such as the embodiments discussed above including shaft 44 and a target tissue localization device disclosed in U.S. Pat. No. 6,179,860.

FIGS. 31-39 illustrate further aspects of the invention in which tissue separator assembly 10 is combined with an elongated coupler 220 and a tissue localization assembly 222 to arrive at a tissue localizing and separating assembly 224. Tissue localization assembly 222 may be of the type disclosed in U.S. Pat. No. 6,179,860. Assembly 222 is shown deployed within a patient 226 with localization device to 112 in a radially expanded, deployed condition. Assembly 222 includes a sheath 228 (see FIG. 32) within which a pull wire 230 is slidably housed. The relative axial movement of sheath 228 and pull wire 230 causes localization device 112 to radially expand and radially contract. The proximal end 232 of pull wire 230 is a recurved end 232 (see FIGS. 32, 34) for engagement by coupler 220 as discussed below.

Coupler 220 is a flexible wire having a coupler loop 234 at its distal end and an enlarged proximal end 236. Coupler 220 passes through shaft 44 (see FIGS. 2, 32) of catheter assembly 12. Coupler loop 234 is used to join coupler 220 to the recurved end 232 of pull wire 230; this is shown in FIGS. 31-34. After being so joined, tissue separator assembly 10 is moved distally along coupler 220, while the user grasps end 236 to maintain tension on the tissue localization assembly 220, causing the joined ends 232, 234 to pass into shaft 44 thus docking tissue localization assembly 222 to tissue separator assembly 10. Continued distal movement of assembly 10 causes catheter assembly 12 to enter patient 226 and pass along the tissue track created by tissue localization assembly 222 until tip 136 of distal portion 46 of shaft 44 is properly positioned relative to localization device 112. Proper positioning is visually indicated to the user by a length of tube 233, typically colored red and affixed to coupler 220, becoming exposed after exiting the proximal end opening 235 of handle 14 as shown in FIGS. 35A-35C. When properly positioned, see FIG. 35C, a locking spring clip 237, located on handle 14 adjacent to proximal end opening 235, springs back from its biased position of FIG. 35B to its unbiased position of FIGS. 35A and 35C to prevent tube 237 from inadvertently reentering handle 14. When so positioned, tissue localization assembly 222 becomes at least temporarily locked or fixed to tissue separator assembly 10 to prevent the inadvertent relative axial movement between localization device 112 and assembly 10. Of course other locking mechanisms, such as a spring finger carried by assembly 220 and engageable with handle 14, can also be used to lock assemblies 10, 222 to one another.

Figure 35:
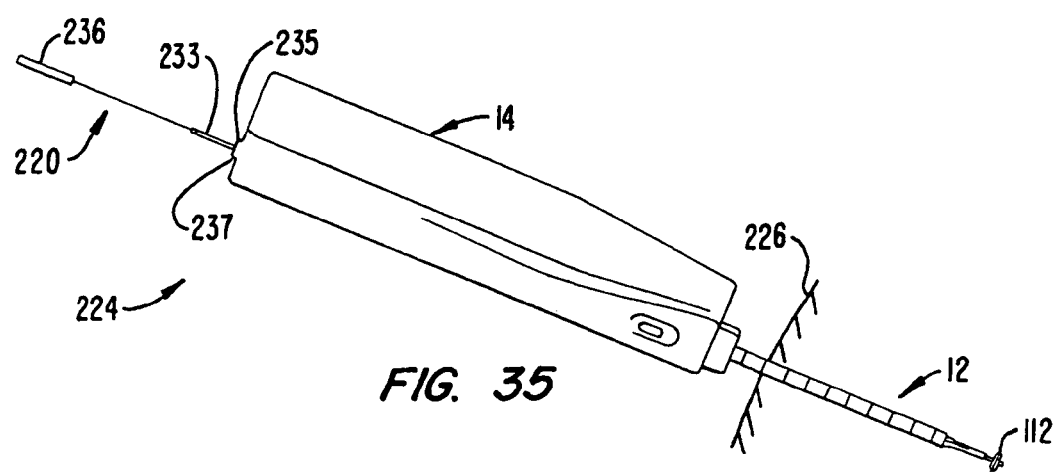
FIG. 35 illustrates the distal movement of the tissue separator assembly causing the joined ends of FIGS. 33 and 34 to be moved into the catheter assembly thereby docking the tissue localization assembly to the tissue separator assembly.
Figure 34:
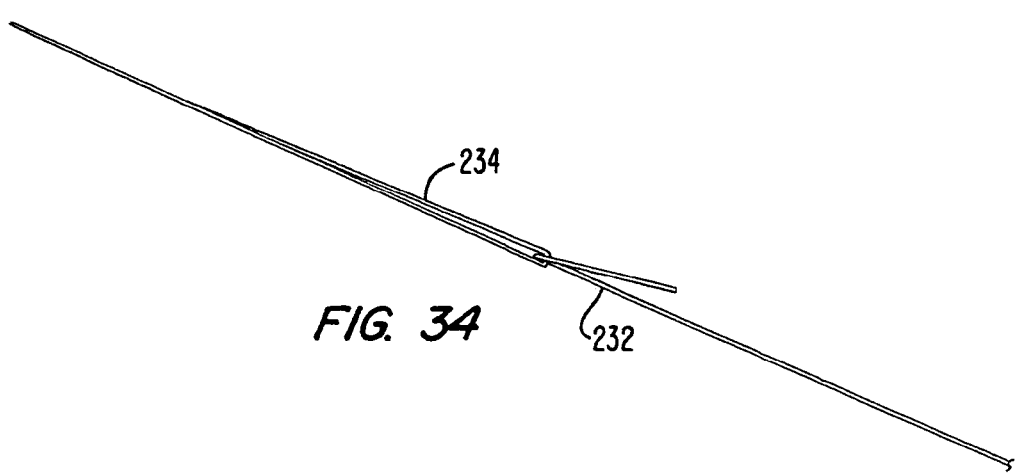
Figure 35A:
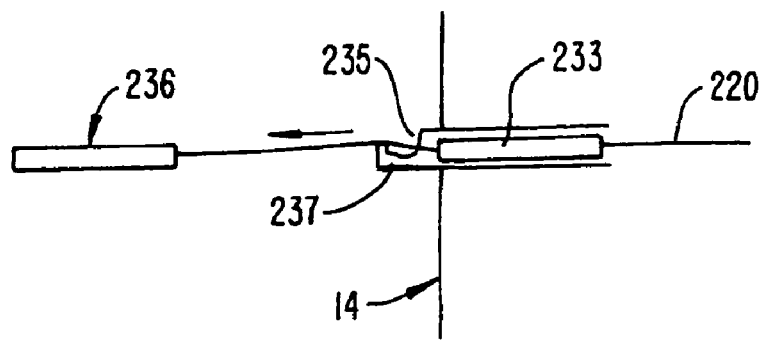
FIGS. 35A-35C are simplified drawings showing the movement of an indicator tube, secured to the elongate coupler, through an opening in the proximal end of the handle.
Figure 35B:
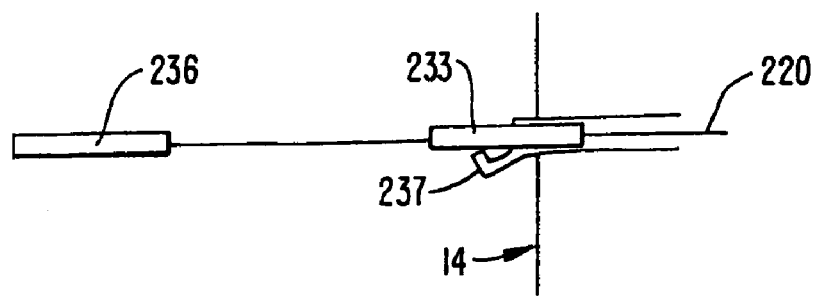
Figure 35C:
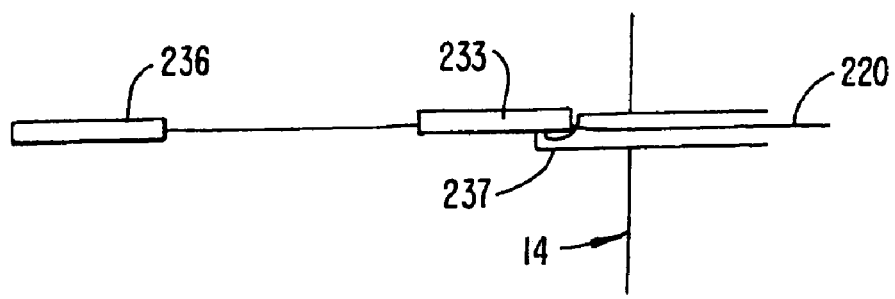
Figure 36:
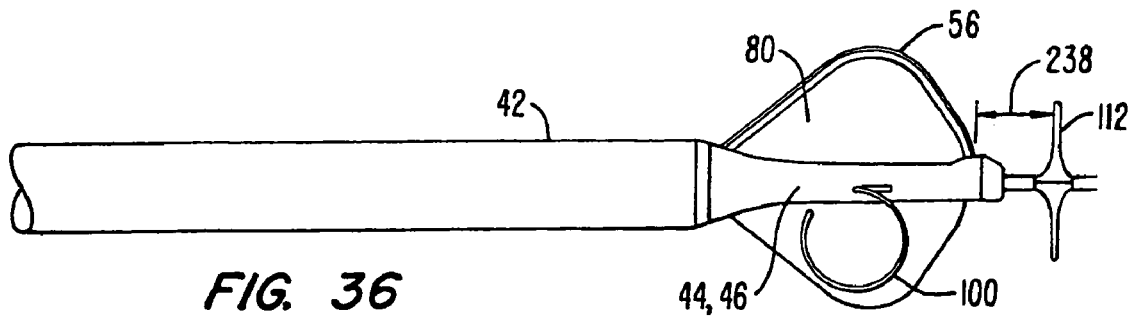
FIG. 36 is an enlarged view of the distal portion of the assembly of FIG. 35 after the separator wire portion has been radially expanded and rotated and after the hook wire has been deployed to engage the separated tissue section.
Figure 37:
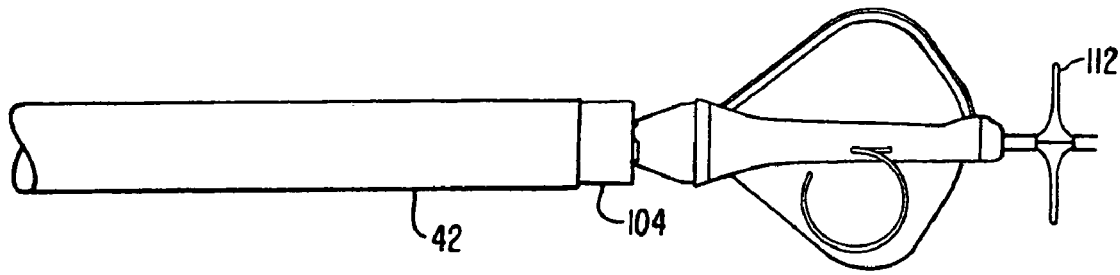
FIG. 37 illustrates the assembly of FIG. 36 after the catheter assembly sleeve has been moved proximally a short distance to expose the distal end of the tubular braided element.
Figure 38:
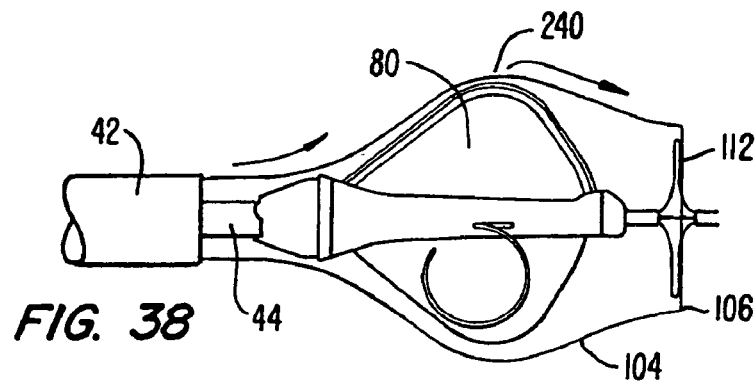
FIG. 38 is a somewhat idealized illustration of the movement of the tubular braided element in a distal direction within a patient with the tubular braided element initially generally following the outline of the separated tissue section and its outer end generally axially aligned with the localization device.

FIG. 36 is an enlarged view of the distal portion of assembly 224 of FIG. 35 after separator wire portion 56 has been radially expanded and rotated, to create a separated tissue section 80, and after hook wire 100 has been deployed to engage the separated tissue section 80. It has been found to be desirable to leave a space, indicated generally as distance 238, between localization device 112 and separated tissue section 80. FIG. 37 illustrates the assembly of FIG. 36 after introducer sheath 42 has been moved proximally a short distance to expose outer end 106 of tubular braided element 104. FIG. 38 is a somewhat generalized illustration of the movement of tubular braided element 104 in a distal direction within patient 226 with the tubular braided element initially generally following the outline of separated tissue section 80 and outer end 106 generally axially aligned with localization device 112. It should be noted that the movement of outer end 106 of tubular braided element 104 will generally following the path indicated until it reaches position 240. Following position 240, the path outer end 106 takes will largely depend on the physical characteristics of the tissue through which is passing. However, the path illustrated is typical. Separated tissue section 80 is then removed from patient 226 by simultaneously pulling the entire assembly shown in FIG. 38, including separated tissue section 80 captured by tubular braided element 104 and localization device 112, secured by coupler 220, back along the tissue track. During this movement tubular braided element 104 has a tendency to elongate axially to a reduced diameter, more cylindrical form thus reducing potential tissue trauma along the tissue track and through the access opening at the beginning of the tissue track.

Figure 39:
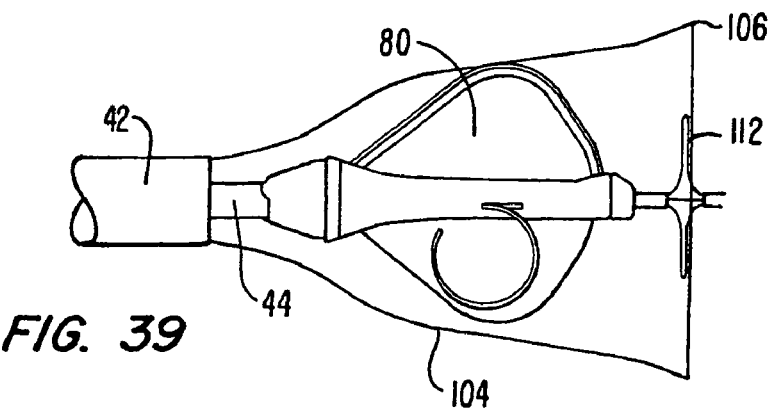
FIG. 39 illustrates the assembly of FIG. 38 after having been removed from the patient with the outer end of the tubular braided element returned to its relaxed state.

FIG. 39 illustrates the assembly of FIG. 38 after having been removed from patient 226 with outer end 106 of tubular braided element 104 returned to its relaxed state and tissue specimen 80 retained by tubular braided element 104 and localization device 112. As suggested in FIG. 39, tubular braided element 104, when in a relaxed state, has a generally trumpet shape with outer end 106 flaring outwardly. It has been found that this trumpet shape helps to guide tubular braided element 104 around separated tissue section 80, especially during its initial movement from introducer sheath 42.

FIGS. 40-45 illustrate a preferred method of making tubular braided element 104. Tubular braided element 104 is sized according to the size of the tissue specimen being removed so that the number of elements, sizes and other specifications discussed below may be varied according to a particular circumstance. FIG. 40 illustrates the shape of a length of tubular braided material 244 after it has been stretched over a cylindrical mandrel (not shown) having an enlarged (20.5 mm diameter by 50 mm long) central portion in this embodiment. Material 244, prior to being stretched over the mandrel, is supplied in a continuous length and cut to size for the mandrel and a starting diameter of ⁵⁄₁₆" or ~8 mm. Material 244 is made of monofilament polyester fibers having a diameter of 0.10 inch (0.25 mm) The braid consists of 56 monofilaments and is made on 56 carrier braider. The braid, when formed in continuous lengths, maintains an approximate ⁵⁄₁₆" (8 mm) internal diameter. The braid angle is held fixed during the braiding operation, and was chosen for this application because a small shortening in axial length results in a rapid change in diameter. The enlarged central portion of the mandrel corresponds to the shape of tubular braided material 244, that is it is cylindrical with generally hemispherical ends. FIG. 41 illustrates the structure of FIG. 40 after one end of the mandrel and tubular braided material 244 has been dipped into a silicone compound. The dipped structure is then cured, typically in an oven, to create a silicone film or web 246 covering one end of tubular braided material 244. After curing, the dipped, cured structure 248 is removed from the mandrel by being pulled over the mandrel from left to right in FIG. 41. FIG. 42 illustrates the open mesh end 250 of the dipped, cured structure 248 being pulled back into the dipped end to create the dual-wall tubular braided element 104 shown in FIG. 43. FIG. 43 illustrates tubular braided element 104 being mounted to the distal end of actuator tube 43. FIGS. 44 and 45 show the proximal end of tubular braided element 104 being secured to the distal end of actuator tube 43 by a length of heat shrink tubing 252 and an adhesive to create a tissue-surrounding assembly 254. Dual-wall tubular braided element 104 has an outer wall 256 substantially completely covered with silicone web 246, and inner wall 258 at least substantially free of the silicone web material, an open outer end 106 covered with silicone web 246.

Silicone web 246 serves at least two functions. It helps maintain the trumpet shape of tubular braided element 104 in its relaxed state while permitting the tubular braided element to radially expand and radially contract from the trumpet shape. It also helps to prevent passage of tissue through tubular braided element 104 during removal of separated tissue section 80. This helps to prevent contamination along the tissue track during tissue removal procedures. While tubular braided element 104 could be made as a single layer, that is without open mesh end 250 being pulled back into the structure, it has been found that doing so helps to maintain a softer leading edge at outer end 106 of tubular braided element 104. The general trumpet shape shown in FIGS. 43-45 occurs as a natural result of the forming process illustrated and described.

The following discussion of the development of the current embodiment of braided element 104 may be useful in appreciating its various features and advantages. The presently preferred embodiment of braided element 104 comprises a tubular sleeve of braided polyester (PET—polyethylene terephthalate) monofilament folded over itself to form a smooth end. The open weave construction allows it to enlarge to several times its original diameter. The outer braided layer is coated with silicone.

Early braided element prototypes consisted of Nitinol braided tubing. The wire diameter, braid angle and number of wires that comprise the braid were explored. These properties affect the strength of the braided element. The braided element must have enough stiffness and columnar strength to overcome the forces acting against it as it is deployed in the tissue. However, if it is too rigid, it may push the separated tissue section further into the cut cavity. Non-braided forms were also considered, such as Nitinol wire placed axially along the lengths of the axis, supported by coating or other rigid members. The combination of wire diameter, braid angle, and number of wires also affects the retracted properties of the braided element. In its undeployed state, the braided element was designed to fit inside a 6 mm sheath. Some of the Nitinol prototypes that were fabricated seemed to have adequate strength and stiffness, and fit within a 6 mm sheath. However, because of other factors discussed below, a PET braid presently preferred over a Nitinol braid.

There are several factors that interact to effect columnar strength. Braid angle, number of filaments, and filament material stiffness and diameter are the main determinants. Axial orientation, greater number and stiffer filaments all combine for greater columnar strength. The presently preferred material for braided element 104 is 0.010" (0.25 mm) diameter monofilament. The number of monofilaments in the braid was chosen to optimize the mechanical properties of braided element 104. Increasing the number of filaments will create the opposite effect—the columnar strength will be reduced thus increasing the chance of buckling. Fewer filaments creates an increase in spacing between the filaments as the braided element expands from retracted to deployed. If the spacing becomes too large, the coating may tear. Also, a braided element constructed with a more axially oriented braid angle will take up much more length in the retracted state and therefore require a greater amount of travel to deploy. The number of filaments was chosen to optimize braided element strength, spacing between filaments, and amount of deployment travel.

It is presently preferred that the distal end of the braided element, that is the end that first comes into contact with the tissue, be smooth. It was discovered at a braided element with jagged or sharp edge may get caught in the tissue and fail to slide into the cut tissue interface around the separated tissue section. For the Nitinol braid, various methods of terminating the lose wires were explored, such as soldering, brazing, or bonding balls at the wire ends, or folding each single wire over. These methods were not very successful. For the balls to be atraumatic, they need to be of considerable size. The balls or folded-over ends increase the diameter of the retracted braided element, making it difficult to fit inside a sheath. This led to concepts of 'roll-over' and 'double layer' braided elements. For both concepts, the tubular braid is folded over itself to form a two-layered braided element with folded-over, smooth ends. For a 'double layer' braided element, the two layers are bonded together at the proximal end. The two-layered Nitinol braided elements that were prototyped showed promising characteristics. However the folded-over ends provided too much bulge and made it difficult or impossible to retract into a 6 mm diameter sheath. The PET braid, on the other hand, forms a nice crease when the braid is folded over, and is easily retracted into the sheath. For deployment, the outer layer is pushed forward and allowed to slide over the inner layer. This embodiment has potential but is not the presently preferred embodiment.

The shape of the braided element also affects its functionality. Braided element prototypes of many different shapes were tested, such as "bullet", "cone", and "bell" or "trumpet" profiles of varying diameters. A desirable characteristic of braided element 104 is that the braided element flares open as it is initially deployed, so that it is predisposed to expand around the biopsy sample rather than push the sample further into the cavity. The shape of braided element 104 has been optimized to maximize the amount that it flares open during deployment.

The braided element is currently coated with a two-component silicone elastomer. Some polyurethane coatings were investigated also, but did not perform as well as silicone coatings during preliminary testing. The silicone coating was chosen because of its high tear strength and elasticity. From the retracted state to the fully deployed state, the diameter of braided element 104 may expand as much as 300%. The braided element may have a snare at the distal end to aid in capturing the sample.

Modification and variation can be made to the disclosed embodiments without departing from the subject of the invention as defined in the following claims. For example, lead screw 52 could be hollow to permit actuator shaft 114, or other medical devices, to pass therethrough and into a lumen within shaft 44. While base surface 150 is shown to have a smoothly curving shape, surface 150 may have other shapes, such as a discontinuous surface shape, a flat surface shape with one or more projections providing the desired bow in the separator wire portion 56, or a combination thereof. Braided element 104 may be made of other materials and by other processes than those disclosed.

Any and all patents, patent applications and printed publications referred to above are hereby incorporated by reference.

What is claimed is:

1. A tissue localizing and separating assembly comprising:
   a tissue separator assembly comprising:
      an elongate tubular member comprising a proximal end, a distal end, and a lumen therebetween;
      a tissue separator device located near the distal end of the elongate tubular member;

an elongate coupler extending through the lumen of the elongate tubular member and having a distal coupler end; and a tissue localization assembly comprising an elongate member and a localization device, wherein the elongate member has a proximal end and a distal end, and wherein the localization device is located at the distal end of the elongate member;

wherein the distal coupler end and the proximal end of the elongate member of the tissue localization assembly are joinable to one another to permit the distal coupler end and the proximal end of the elongate member of the tissue localization assembly to be joined and moved into the lumen of the elongate tubular member thereby docking the tissue localization assembly to the tissue separator assembly.

2. The assembly according to claim 1, wherein the tissue separator device comprises a distal separator part movable between a retracted state, towards the elongate tubular member, and a radially operational state, away from the elongate tubular member.

3. The assembly according to claim 2, wherein the tissue separator assembly further comprises an introducer sheath within which the elongate tubular member is rotatably mounted and wherein the distal separator part is movable radially outwardly to the operational state.

4. The assembly according to claim 1, wherein the elongate coupler comprises a flexible wire and the distal coupler end comprises a wire loop.

5. The assembly according to claim 1, wherein the tissue localization assembly is movable from a first, radially-contracted state to a second, radially-expanded state.

6. The assembly according to claim 5, wherein the tissue localization assembly comprises a hollow sheath housing a pull wire, the pull wire having a recurved end constituting said proximal localization assembly end.

7. The assembly according to claim 1, wherein the tissue separator assembly comprises a proximal end opening through which the elongate coupler passes.

8. The assembly according to claim 1, wherein the tissue separator assembly further includes a handle, the handle having a proximal end opening.

9. The assembly according to claim 1, wherein the elongate coupler includes an engagement element engageable with the tissue separator assembly when the distal separator device is adjacent to the localization device.

10. The assembly according to claim 9, wherein the engagement element comprises a spring element carried by the elongate coupler.

11. The assembly according to claim 1, wherein the tissue separator assembly comprises:

a tissue-energizing circuit comprising an energy source and a force-sensitive switch selectively coupling the tissue separator device to the energy source; and said force-sensitive switch operably coupled to the tissue separator assembly so that when a driving force applied to the tissue separator device exceeds a level, said switch closes permitting energy from the energy source to reach the distal end of tissue separator device, thereby aiding passage of the tissue separator device through the tissue.

12. A method for docking a tissue separator assembly to a tissue localization assembly comprising:

providing a tissue separator assembly comprising an elongate tubular member and a tissue separator device, wherein the elongate tubular member comprises a proximal end, a distal end, and a lumen therebetween, and the tissue separator device is located near the distal end of the elongate tubular member;

directing a tissue localization assembly along a tissue track to a position at a target site, the tissue localization assembly comprising an elongate member and a localization device, wherein the elongate member has a proximal end and a distal end, and wherein the localization device is located at the distal end of the elongate member;

changing the localization device from a first, radially-contracted state to a second, radially-expanded state;

joining a distal end of an elongate coupler to the proximal end of the elongate member of the tissue localization assembly, the elongate coupler passing through the lumen of the elongate tubular member of the tissue separator assembly; and moving the joined proximal and distal ends into the lumen of the elongate tubular member of the tissue separator assembly, thereby docking the tissue localization assembly and the tissue separator assembly.

13. The method according to claim 12, wherein the joining step comprises engaging a coupler loop at the distal end of the elongate coupler to a recurved element at the proximal end of the tissue localization assembly.

14. The method according to claim 12, wherein the directing step is carried out so that the localization device is directed to a position distal of the target site.

* * * * *